United States Patent
Nowak

(10) Patent No.: US 12,004,733 B2
(45) Date of Patent: *Jun. 11, 2024

(54) SURGICAL RETRACTOR SYSTEM AND CLIP-ON JOINT CLAMP

(71) Applicant: Thompson Surgical Instruments, Inc., Traverse City, MI (US)

(72) Inventor: Steve Nowak, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/134,548

(22) Filed: Apr. 13, 2023

(65) Prior Publication Data

US 2023/0248344 A1    Aug. 10, 2023

Related U.S. Application Data

(63) Continuation of application No. 17/484,020, filed on Sep. 24, 2021, now Pat. No. 11,633,180.

(51) Int. Cl.
*A61B 17/02* (2006.01)
*A61B 90/57* (2016.01)

(52) U.S. Cl.
CPC .......... *A61B 17/0206* (2013.01); *A61B 90/57* (2016.02)

(58) Field of Classification Search
CPC .............. A61B 17/0206; A61B 17/645; A61B 17/6458; A61B 17/6466; A61B 17/6416; A61B 90/56; F16B 2/10; F16B 2/18; F16B 2/185; F16B 7/04; F16B 7/0426; F16B 7/0433; F16B 7/044; F16B 7/048; F16B 7/0493

See application file for complete search history.

(56) References Cited

U.S. PATENT DOCUMENTS

| | | | |
|---|---|---|---|
| 2,893,378 A | 7/1959 | Cooper | |
| 3,221,743 A | 12/1965 | Thompson et al. | |
| 3,965,890 A | 6/1976 | Gauthier | |
| 4,421,108 A | 12/1983 | Cabrera et al. | |
| 4,596,484 A | 6/1986 | Nakatani | |
| 4,617,916 A | 10/1986 | LeVahn et al. | |
| 4,700,437 A * | 10/1987 | Hoshino | B25B 5/04 984/150 |
| 4,813,401 A | 3/1989 | Grieshaber | |
| 4,971,038 A | 11/1990 | Farley | |
| 5,020,195 A | 6/1991 | LeVahn | |
| 5,025,780 A | 6/1991 | Farley | |

(Continued)

*Primary Examiner* — Julianna N Harvey
*Assistant Examiner* — Anna V. Little
(74) *Attorney, Agent, or Firm* — McAndrews, Held & Malloy, Ltd.

(57) ABSTRACT

A joint clamp for a surgical retractor system includes clamps, a cam bolt, and a cam lever. The cam bolt passes through the clamps. A cam lever comprising a cam head pivotally attached an upper portion the cam bolt to permit rotation between a locked position and an unlocked positions. The joint clamp may include springs which provide a scissors clamp of the clamps with a clip-on feature in which the scissors clamp may clipped-on and clipped-off an object such as a frame member, table post, or retractor handle. The springs may further prevent or reduce a rising movement of the clamps when the cam lever rotates from an unlocked state to a locked state.

30 Claims, 15 Drawing Sheets

(56) References Cited

U.S. PATENT DOCUMENTS

| | | |
|---|---|---|
| 5,224,680 A | 7/1993 | Greenstein et al. |
| 5,515,744 A | 5/1996 | Liao |
| 5,609,565 A | 3/1997 | Nakamura |
| 5,846,192 A | 12/1998 | Teixido |
| 5,897,087 A | 4/1999 | Farley |
| 6,033,363 A | 3/2000 | Farley et al. |
| 6,254,532 B1 | 7/2001 | Paolitto et al. |
| 6,302,843 B1 | 10/2001 | Lees et al. |
| 6,474,900 B2 | 11/2002 | Feng |
| 6,511,423 B2 | 1/2003 | Farley |
| 6,610,009 B2 | 8/2003 | Person |
| 7,125,380 B2 | 10/2006 | Yager |
| 7,297,107 B1 | 11/2007 | Bjork et al. |
| 7,320,666 B2 | 1/2008 | Bjork et al. |
| 7,338,442 B2 | 3/2008 | Mulac et al. |
| 7,553,279 B1 | 6/2009 | Phillips et al. |
| 7,556,229 B2 | 7/2009 | Elliott et al. |
| 7,562,855 B2 | 7/2009 | Oetlinger |
| 7,749,163 B2 | 7/2010 | Mulac et al. |
| 7,758,502 B2 | 7/2010 | Phillips et al. |
| 8,057,467 B2 | 11/2011 | Faller et al. |
| 8,172,840 B2 | 5/2012 | Mürner et al. |
| 8,696,562 B2 | 4/2014 | Mulac et al. |
| 9,089,299 B2 | 7/2015 | Nowak et al. |
| 9,636,785 B2 | 5/2017 | Traver et al. |
| 2002/0177754 A1 | 11/2002 | Phillips |
| 2003/0229272 A1* | 12/2003 | Mulac ............... A61B 17/02 600/234 |
| 2003/0229273 A1 | 12/2003 | Mulac et al. |
| 2006/0178566 A1 | 8/2006 | Fetzer |
| 2007/0213597 A1 | 9/2007 | Wooster |
| 2007/0233066 A1* | 10/2007 | Rezach ............ A61B 17/7037 606/252 |
| 2008/0247818 A1 | 10/2008 | Oesch et al. |
| 2008/0312509 A1 | 12/2008 | Jacobson et al. |
| 2009/0013507 A1 | 1/2009 | Scott et al. |
| 2009/0088751 A1* | 4/2009 | Mullaney ......... A61B 17/6466 606/54 |
| 2010/0132163 A1* | 6/2010 | Hasei ................ A01D 34/90 16/421 |
| 2012/0004659 A1* | 1/2012 | Miller ............... A61B 17/60 606/54 |
| 2014/0180017 A1 | 6/2014 | Mulac et al. |
| 2020/0284382 A1* | 9/2020 | Lenz ...................... F16B 2/08 |
| 2021/0196255 A1 | 7/2021 | Farley et al. |

* cited by examiner

SURGICAL RETRACTOR SYSTEM AND CLIP-ON JOINT CLAMP

BACKGROUND OF THE INVENTION

The present invention relates to retractor systems used during surgical procedures.

During surgical procedures, a surgeon typically makes an incision in a patient to access a site of interest for the particular surgical procedure. To maintain clear access to the site of interest, a surgical retractor system is typically utilized. A surgical retractor system typically includes a rail clamp, a frame connected to the rail clamp by a joint clamp, and retractor blades that are connected to the frame by additional joint clamps. The rail clamp is commonly secured to an operating table and provides a fixed and sturdy support for the frame and the retractor blades. Each of the components in a typical surgical retractor system is conventionally made of stainless steel. Other materials such as aluminum and titanium have also been used.

Limitations and disadvantages of conventional and traditional approaches should become apparent to one of skill in the art, through comparison of such systems with aspects of the embodiments set forth in the remainder of the present disclosure.

BRIEF SUMMARY OF THE INVENTION

Surgical retractor systems and joint clamps for such surgical retractor systems are shown in and/or described in at least one figure of the present disclosure. Such surgical retractor systems, joint clamps, and/or other aspects of the present disclosure are set forth more completely in the claims. Advantages, aspects, novel features, as well as, details of illustrated embodiments will be more fully understood from the following description and figures.

DETAILED DESCRIPTION OF THE INVENTION

Figure 1:
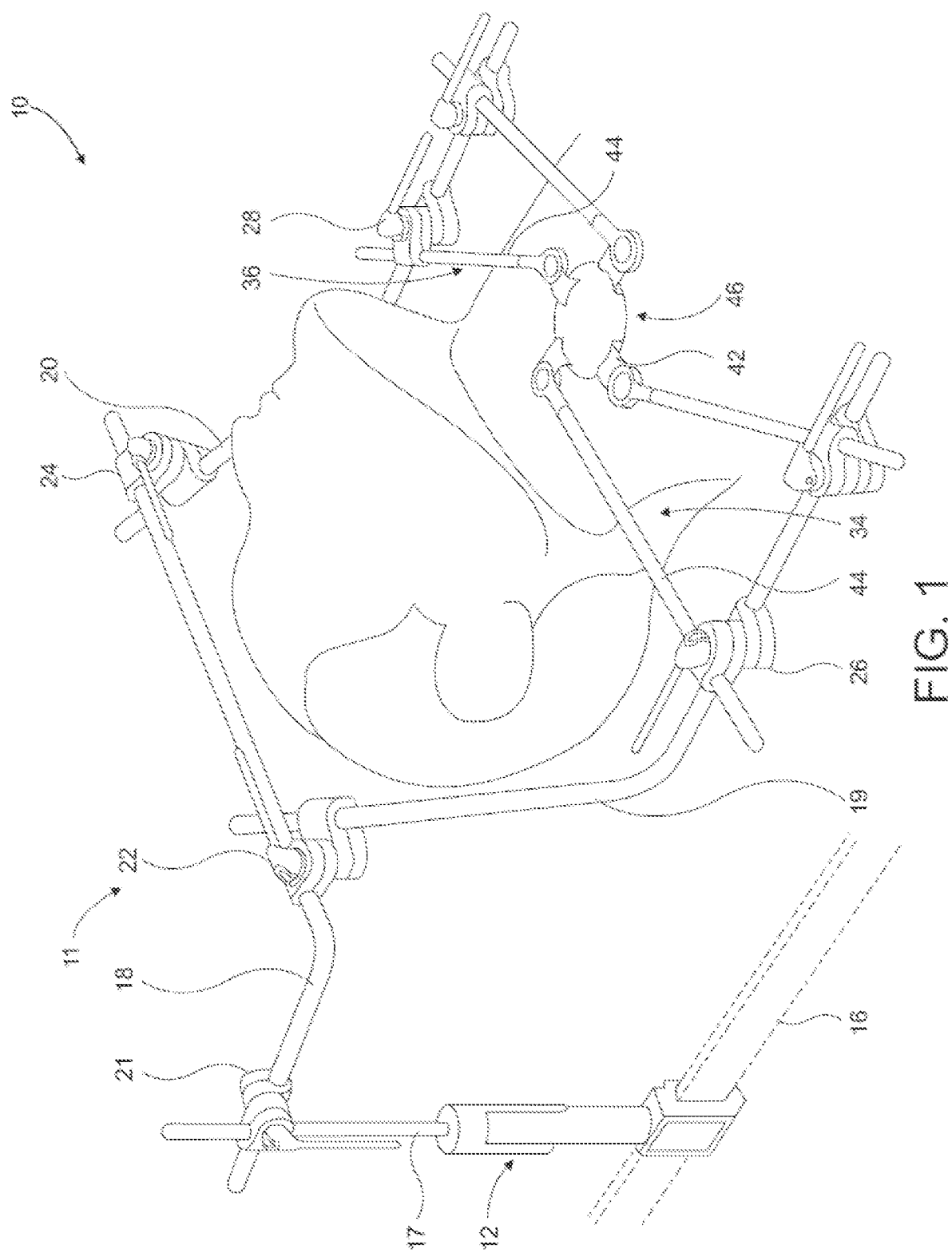
FIG. 1 is a perspective view of a surgical retractor system having joint clamps per one or more embodiments described herein.

Various aspects of the present disclosure are presented by way of example. Such examples are non-limiting, and thus the scope of various aspects of the present disclosure are not necessarily limited by any particular characteristics of the provided examples. In the following, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like specify the presence of stated features, integers, steps, operations, elements, and/or components, but do not preclude the presence or addition of one or more other features, integers, steps, operations, elements, components, and/or groups thereof.

Although the terms first, second, etc. may be used herein to describe various elements, these elements should not be limited by these terms. These terms are only used to distinguish one element from another element. Thus, for example, a first element, a first component, or a first section could be termed a second element, a second component, or a second section without departing from the teachings of the present disclosure. Similarly, various spatial terms, such as "upper," "lower," "side," and the like, may be used in distinguishing one element from another element in a relative manner. However, components may be oriented in different manners without departing from the teachings of the present disclosure. For example, a component may be turned sideways so that its "top" surface faces horizontally and its "side" surface faces vertically.

In the drawings, various dimensions (e.g., thicknesses, widths, lengths, etc.) may be exaggerated for illustrative clarity. Additionally, like reference numbers are utilized to refer to like elements through the discussions of various examples.

Referring now to FIG. 1, a surgical retractor system 10 may include a frame assembly 11. The frame assembly 11 may secure retractor blades 34, 36 to a surgical table 16 to eliminate or reduce movement the retractor blades 34, 36 relative to and the surgical table 16 and a patient on the surgical table 16. To this end, the frame assembly 11 may include adjustable rail clamps 12, posts 17, cross bars 18, extension arms 19, 20, and multi-directional joint clamps 21, 22, 24, 26, 28 (hereafter "joint clamp or joint clamps"). A first adjustable rail clamp 12 may be secured to one side of the surgical table 16. A second adjustable rail clamp (not shown) may be secured to an opposite side of the surgical table 16 for increased stability. A post 17 may extend vertically from the rail clamp 12 to provide support for a cross bar 18 which in turn provides support for a pair of extension arms 19, 20. The cross bar 18 may be secured to the post 17 by a joint clamp 21. The extension arms 19, 20 may be respectively secured to the cross bar 18 by a pair of joint clamps 22, 24. In some configurations, the extension arms 19, 20 may be secured directly to the post 17 by a joint clamp, thus eliminating the cross bar 18 in certain circumstances.

Additional joint clamps 26, 28 may be disposed along the extension arms 19, 20. The joint claims 26, 28 may secure retractor blades 34, 36 to the extension arms 19, 20. Each retractor blade 34, 36 may include a blade portion 42 and a retractor arm 44. The blade portion 42 may extend downwardly into the incision 46 made by the surgeon and may retract anatomical features to improve the surgeon's access via the incision 46 to other anatomical features of the patient.

Figure 2:
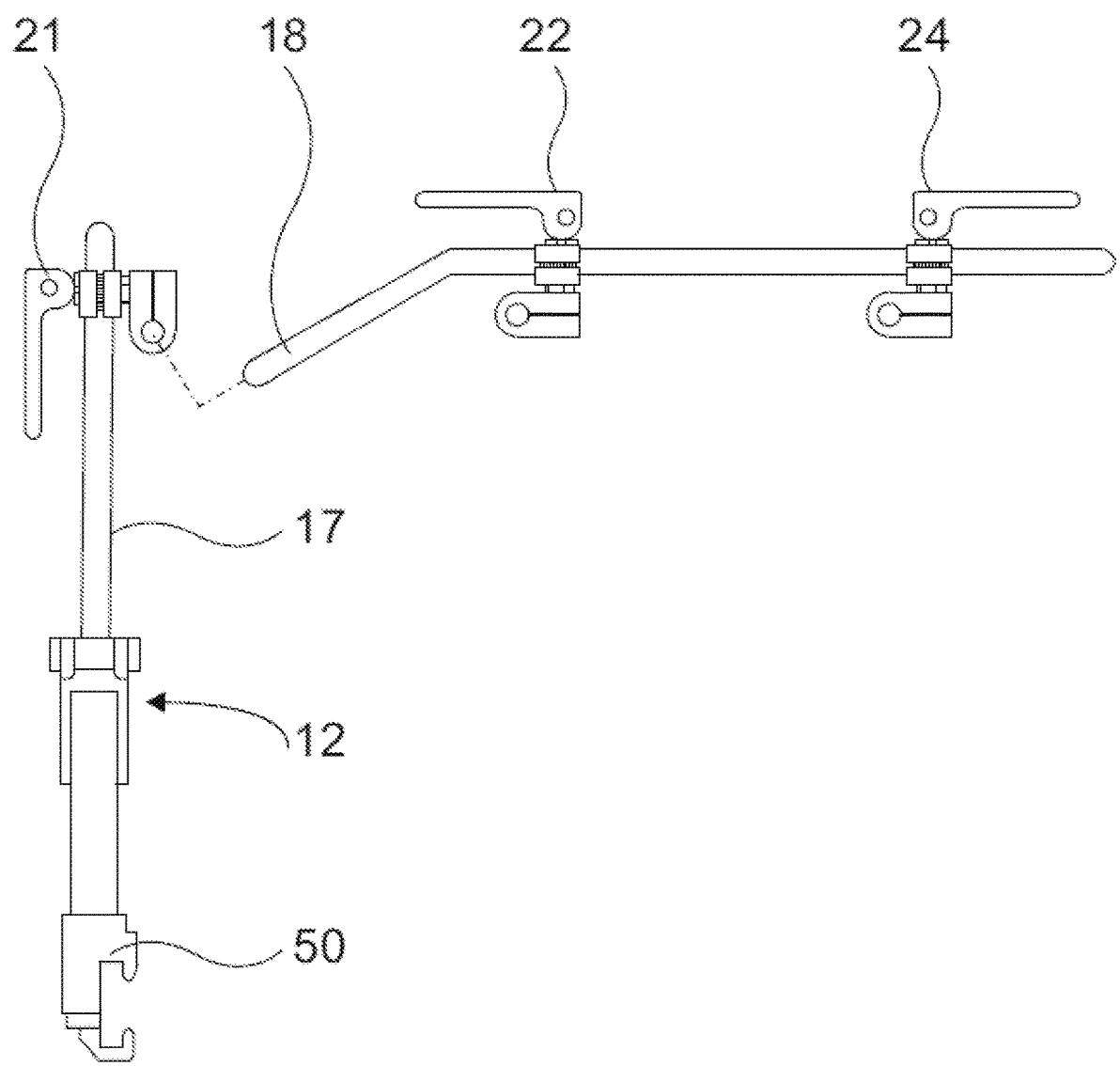
FIG. 2 is an elevated view of the rail clamp, joint clamps, and cross bar of the surgical retractor system shown in FIG. 1.

FIG. 2 provides an another view of the rail clamp 12 and the cross bar 18 of FIG. 1. The rail clamp 12 may include a clamp 50 that may be secured to the surgical table 16 of FIG. 1. The joint clamp 21 is shown at an upper distal end of the post 17. However, the joint clamp 21 may be positioned anywhere along the post 17 so as to position the cross bar 18 at an appropriate height for a surgical procedure. FIG. 2 further shows the joint clamps 22, 24 at respective positions along the cross bar 18. The joint clamps 22 and 24 may be identical to each other or may differ depending on the intended use of each of the clamps 22, 24. Additionally, the joint clamps 22, 24 may each be the same as or differ from the joint clamp 21 on the post 17.

Referring to FIGS. 3-11, a first embodiment of a joint clamp 100 is shown. The joint clamp 100 may be suitable for one or more of the joint clamps 21, 22, 24, 26, 28 of FIGS. 1 and 2. However, clip-on features of the joint clamp 100 may be more suitable for the joint clamps 26, 28 than the other joint clamps of FIGS. 1 and 2 since the joint clamps 26, 28 are used to secure the retractor blades 34, 36 to the extension arms 19, 20.

As shown in FIGS. 3-6, the joint clamp 100 may include a scissors clamp 200, a circle clamp 300, a bushing 400, a cam lever 500, and a cam bolt assembly 600. While depicted with an upper circle clamp 300 and a lower scissors clamp 200, the joint clamp 100 may be implemented with a different quantity and/or arrangement of clamps. For example, the joint clamp 100 may include three or more clamps of various assortments of scissors clamps and/or circle clamps. In another embodiment, the joint clamp 100 may comprise an upper scissors clamp 200 and a lower circle clamp 300.

The cam bolt assembly 600 generally includes a cam bolt 610 that passes through cam bolt holes of the scissors clamp 200, the circle clamp 300, and the bushing 400. An upper end 612 of the cam bolt 610 may be coupled to the cam lever 500. A lower end 616 of the cam bolt 610 may be coupled to a base 620 of the cam bolt assembly 600. In this manner, the clamps 200, 300 are coupled to the cam bolt assembly 600 in a stacked manner between the cam lever 500 and the base 620.

Figure 5:
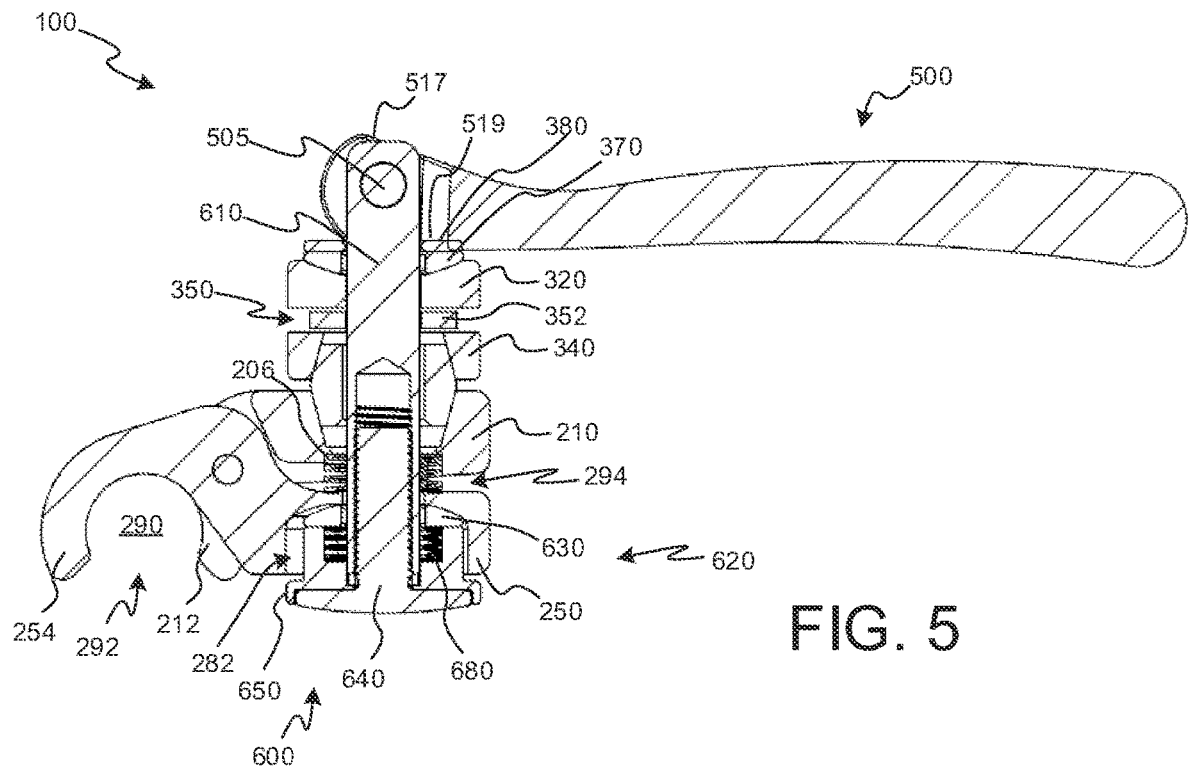
FIG. 5 is a cross-sectional view of the joint clamp shown in FIG. 3 with its cam lever in a locked position.
Figure 6:
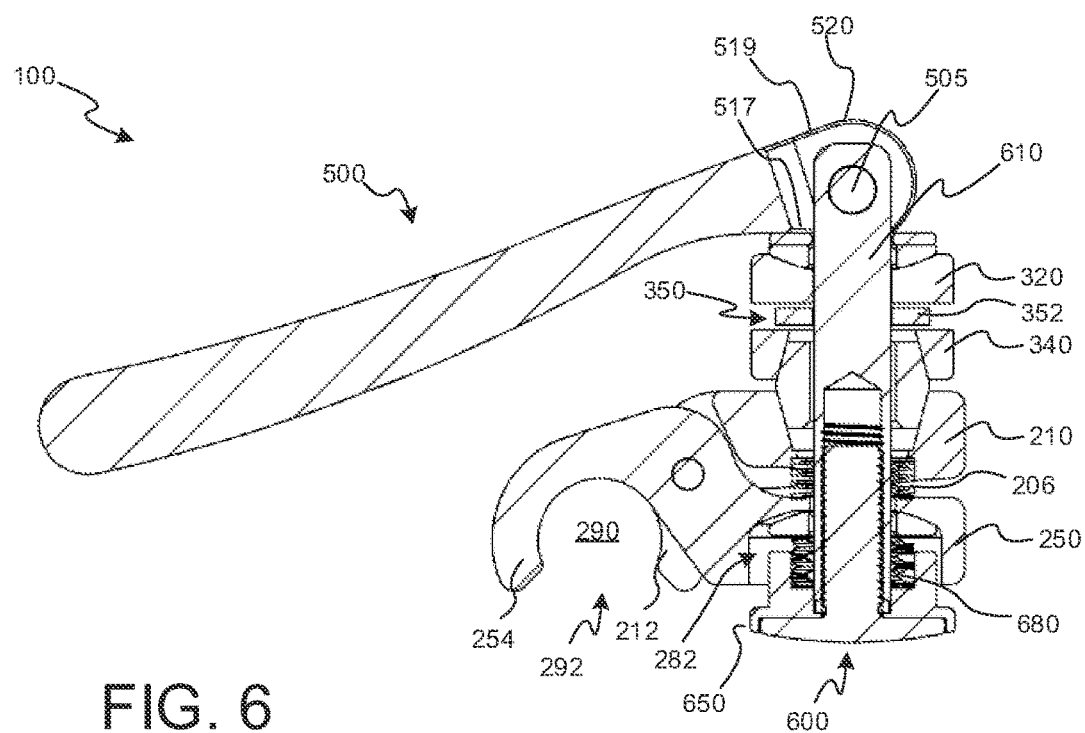
FIG. 6 is a cross-sectional view of the joint clamp shown in FIG. 3 with its cam lever in an unlocked position.
Figure 7:
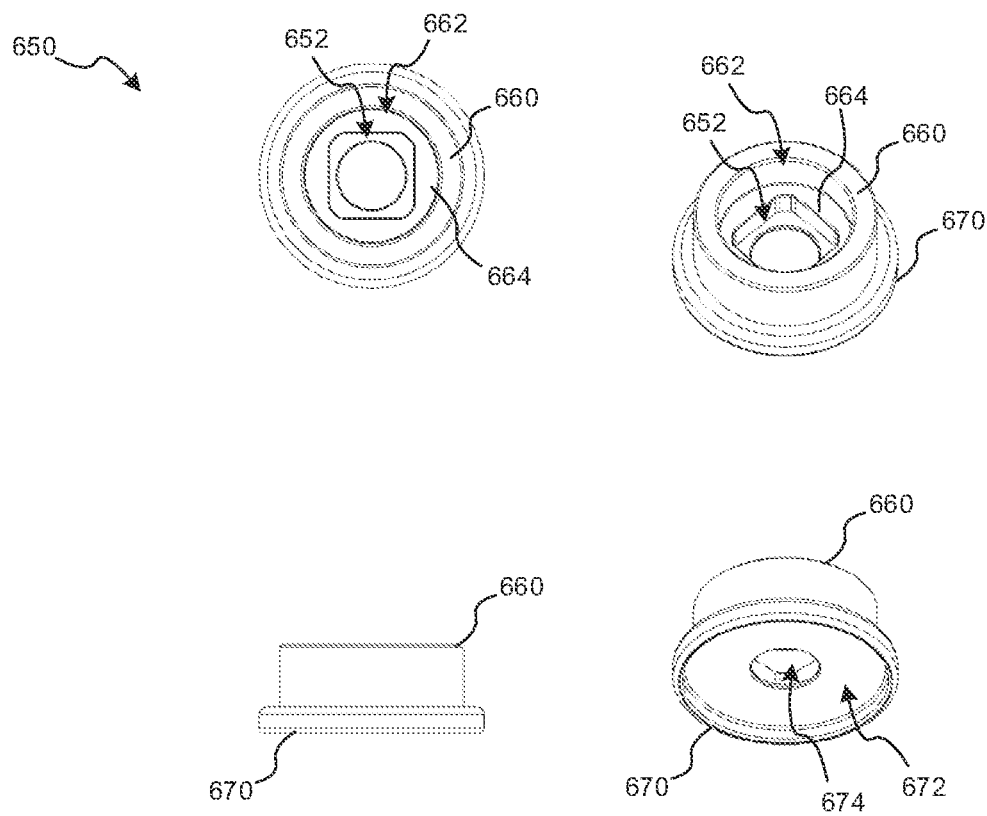
FIG. 7 depicts multiple views of a sleeve of the joint clamp shown in FIG. 3.
Figure 8:
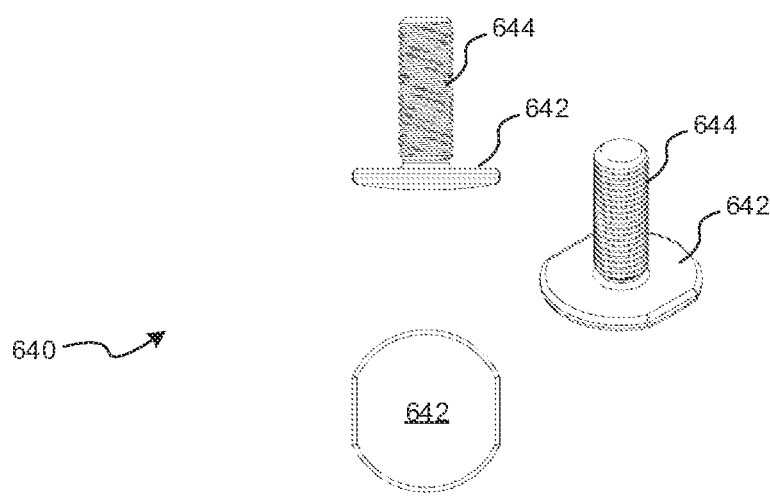
FIG. 8 depicts multiple views of a set screw of the joint clamp shown in FIG. 3.
Figure 9:
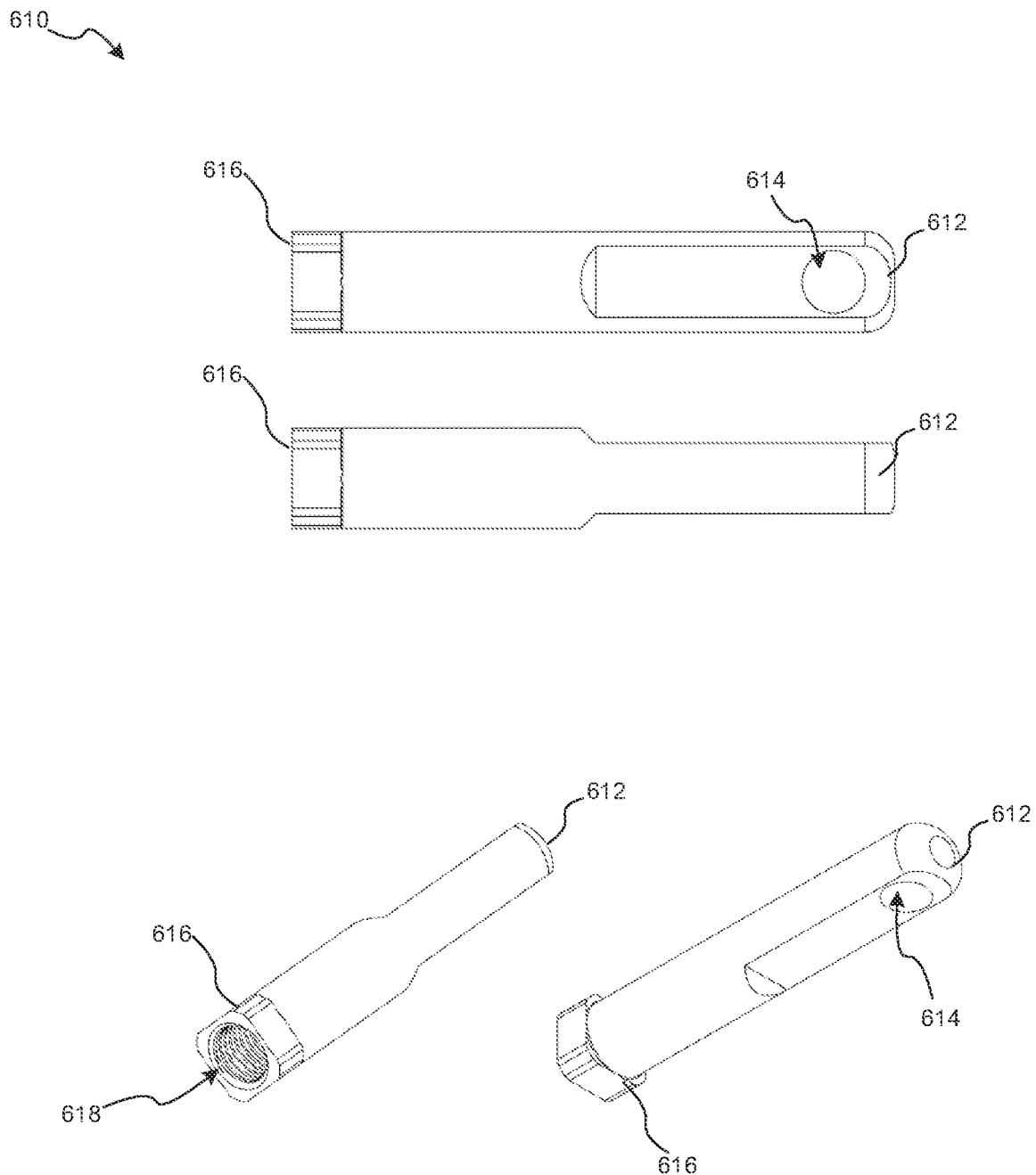
FIG. 9 depicts multiple views of a cam bolt of the joint clamp shown in FIG. 3.
Figure 10:
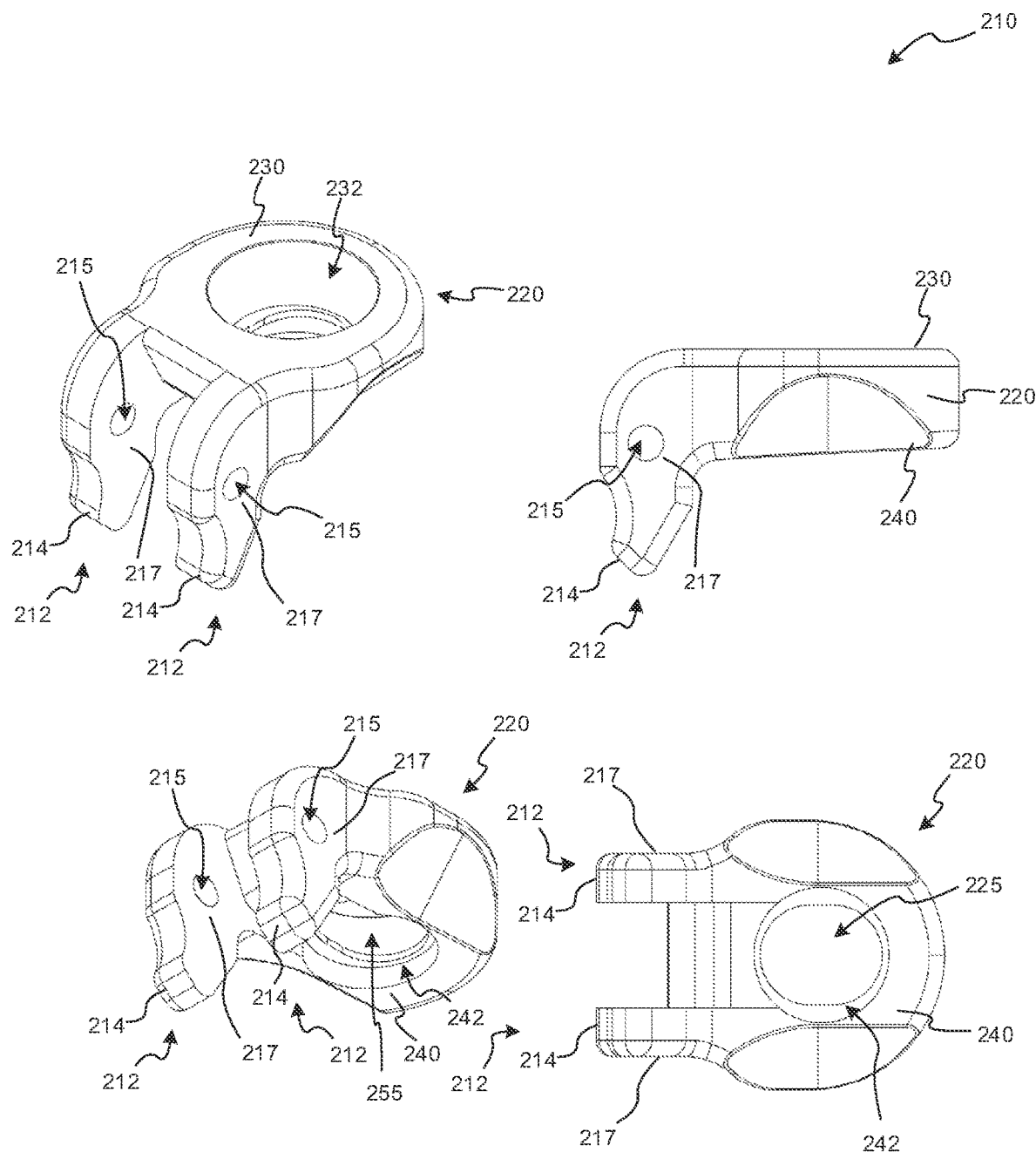
FIG. 10 depicts multiple views of a first scissors portion of the joint clamp shown in FIG. 3.
Figure 11:
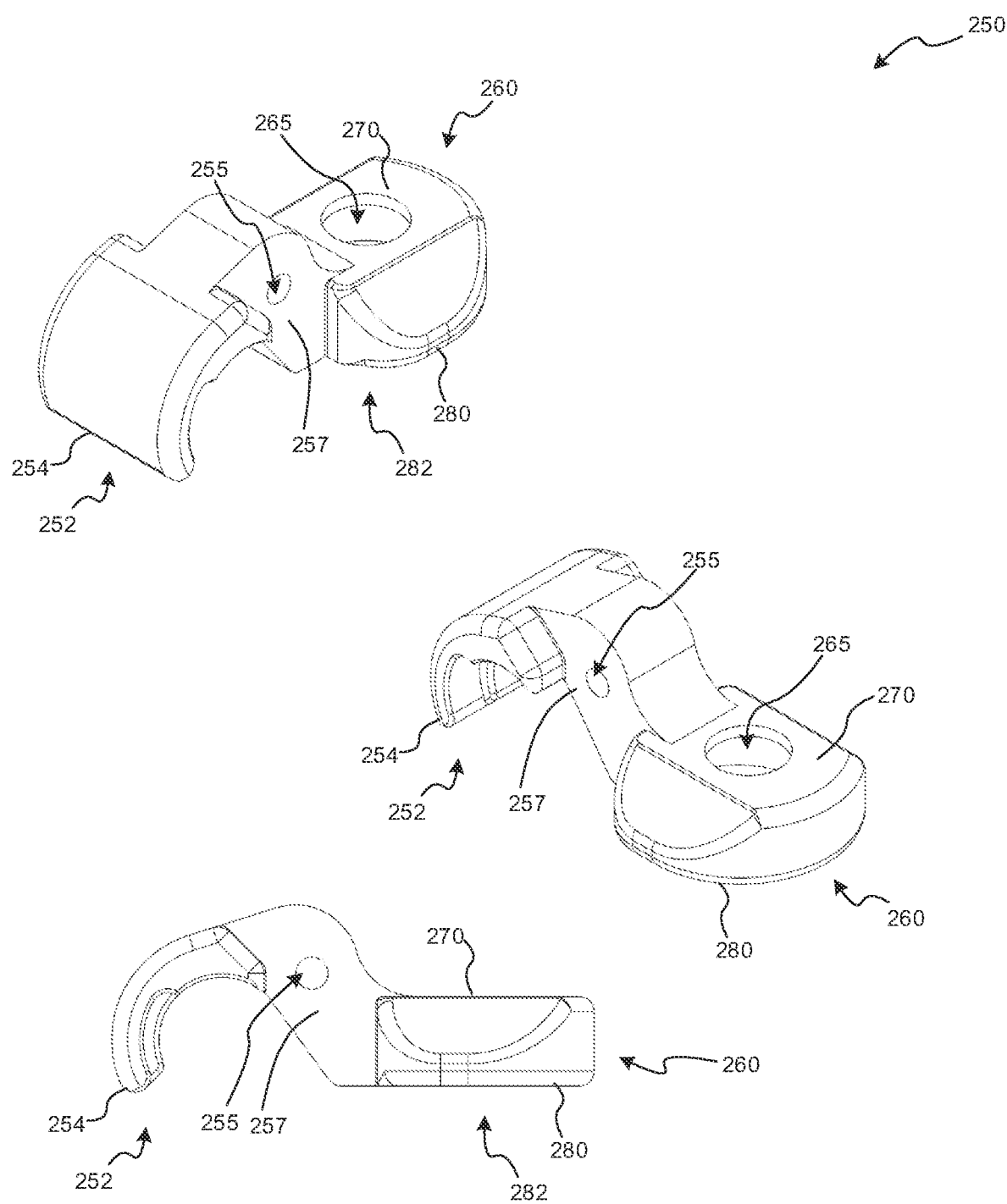
FIG. 11 depicts multiple views of a second scissors portion of the joint clamp shown in FIG. 3.

The cam lever 500 may be rotated between a locked position of FIG. 5 and an unlocked position of FIG. 6. In the locked position, the scissors clamp 200 and the circle clamp 300 each apply a respective clamping force to an object such as, for example, a frame member, a table post, a retractor handle, etc. that passes through the respective clamp 200, 300. In particular, rotation of the cam lever 500 may adjust a distance between a lower surface of the cam head 510 and an upper surface of the base 620. When the cam lever 500 is in a locked position, a lower surface of the cam head 510 is closer to the upper surface of the base 620 than when the cam lever 500 is in an unlocked position. Thus, rotating the cam lever 500 from the unlocked position to the locked position decreases the distance between a lower surface of the cam head 510 and an upper surface of the base 620 which increases a compression force applied by the cam lever 500 and the base 620 to the clamps 200, 300. Such compression of the clamps 200, 300 may cause each of the clamps 200, 300 to apply a respective clamping force to objects passing through their respective clamping passages 290, 390. In general, the clamping force is sufficient to lock or retain the object within clamping passages 290, 390 of the respective clamps 200, 300 and prevent the object from rotating, sliding, or otherwise repositioning with respect to the clamps 200, 300.

Conversely, rotating the cam lever 500 from the locked position to the unlocked position increases the distance between a lower surface of the cam head 510 and an upper surface of the base 620, which reduces or removes a compression force applied by the cam lever 500 and the base 620 to the clamps 200, 300. Such reduction/removal of the compression force causes each of the clamps 200, 300 to reduce or remove forces applied to the object that passes through their respective clamping passages 290, 390. In general, the forces applied by the clamps 200, 300 are sufficiently removed or reduced so as to permit objects to rotate, slide, or otherwise reposition with respect to the clamps 200, 300.

The springs 206, 680 of the scissors clamp 200 may provide the clamp 200 with a clip-on feature. In particular, the spring 206 may bias the jaws 212, 252 of the scissors clamp 200 in an open direction and the spring 680 may bias the jaws 212, 252 in a closed direction. The spring 206 has a greater spring constant than the spring 680. As such, the spring 206 is stiffer than the spring 680 and exerts a greater force than the spring 680. Thus, the bias of the spring 206 overcomes the bias of the spring 680 and biases the mouth opening 292 toward an opened position. However, the spring 206 and the spring 680 are positioned such that the spring 206 reaches its non-compressed or resting state before the mouth opening 292 reaches a position sufficient for an object passing through the clamping passage 290 to escape the clamping passage 290 via the mouth opening 292. In other words, the spring 206 does not increase the mouth opening 292 beyond a diameter of an object in the clamping passage 290 or an object expected to be received by the clamping passage 290. Thus, with the mouth opening 292 in the partially-opened or receiving position, the spring 206 prevents the spring 680 from closing jaws 212, 252 while at the same time the spring 680 biases or prevents the jaws 212, 252 from opening further without the application of an external force.

While the mouth opening 292 is in the partially-opened or receiving position, an object such as a frame member, a table post, a retractor handle, etc. may be pressed against the mouth opening 292 with sufficient force to overcome the compression force of the spring 680 so as to expand the mouth opening 292 and permit the object to pass between the jaws 212, 252 and into a clamping passage 290 defined by the jaws 212, 252. Once passed the jaws 212, 252 and into the clamping passage 290, the spring 680 may bias the jaws 212, 252 back toward the partially-opened position so as to retain the object in the clamping passage 290. Conversely, the object may be pulled from clamping passage 290 of the scissors clamp 200 with sufficient force to overcome the compression force of the spring 680 so as to expand the mouth opening 292 and permit the object to pass between the jaws 212, 252 and out of the clamping passage 290 defined by the jaws 212, 252. Again, once passed the jaws 212, 252, the spring 680 may bias the jaws 212, 252 back toward the partially-opened position. In this manner, the scissors clamp 200 may be clipped-on an object by pushing the scissors clamp 200 against the object with a clip-on force that overcomes the compression force of the spring 680, and the scissors clamp 200 may be removed from the object by pulling the scissors clamp 200 away from the object with a clip-off force that overcomes the compression force of the spring 680. In certain embodiments, the compression force of the spring 680 sufficiently biases the jaws 212, 252 toward the closed direction so as to require the clip-off force to be greater than a gravitational force exerted by the scissors clamp 200. In this manner, the spring 680 and associated clip-off force prevent the scissors clamp 200 from detaching from the object due to its own weight when in the unlocked position.

In addition to the clip-on feature, the spring 680 may also provide the joint clamp 100 with an anti-rise-up feature. FIG. 5 depicts the joint clamp 100 in a locked position. Conversely, FIG. 6 which depicts the joint clamp 100 in an unlocked portion. In comparing the locked state of FIG. 6 to the unlocked state of FIG. 5, it should be apparent that the clamps 200, 300 are longitudinally positioned along the cam bolt 610 at essentially the same location. However, absent the spring 680, the clamps 200, 300 would slide down the cam bolt 610 due to the base 620 moving away from the scissors clamp 200 when in the unlocked position. Of particular note, absent the spring 680, the washer 630 would rest on sleeve 650 in FIG. 6. Thus, when transitioning from the unlocked state of FIG. 6 to the locked state of FIG. 5, the clamps 200, 300 may rise with the base 620 if the spring 608 were not present. Such rise in the clamps 200, 300 may move or adjust objects such as retractors coupled to the clamps 200, 300, which could be detrimental to the patient. However, as shown in FIG. 6, when the cam lever 500 is in the unlocked position, the spring 680 help take up the slack introduced due the reduced compressive forces between the cam lever 500 and the base 620. As a result, the spring 680 may prevent or reduce any such rise-up of the clamps 200, 300, when transitioning the cam lever 500 from the unlocked state of FIG. 6 to the locked state of FIG. 5.

With reference to FIGS. 3-6, 10, and 11, further details regarding the scissors clamp 200 are provided. The scissors clamp 200 may include a first scissors portion 210 and a second scissors portion 250. The first scissors portion 210 may include an upper handle 220 of the scissors clamp 200. The upper handle 220 may include an upper surface 230 and a lower surface 240. The upper surface 230 may include an upper recess 232. The upper recess 232 may include a frustoconical surface configured to engage the frustoconical lower surface 420 of the bushing 400. The lower surface 240 may include a lower recess 242. The lower recess 242 may include one or more surfaces configured to receive and retain an upper end of the compression spring 206.

Furthermore, the first scissors portion 210 may include a cam bolt hole 225 that passes vertically through the upper handle 220. In one embodiment, the upper recess 232, the cam bolt hole 225, and the lower recess 242 are coaxially aligned with one another so as to permit the cam bolt 610 to pass through the upper recess 232, the cam bolt hole 225, the lower recess 242, and the spring 206 seated in the lower recess 242. To this end, the cam bolt hole 225 may have a diameter greater than a diameter of the cam bolt 610, the upper recess 232 may have a diameter greater than a diameter of the bushing 400, and the lower recess 242 may have a diameter greater than a diameter of the spring 206.

The second scissors portion 250 may include a lower handle 260 of the scissors clamp 200. The lower handle 260 may include an upper surface 270 and a lower surface 280. The upper surface 270 may include one or more surfaces configured to engage a lower end the compression spring 206. The lower surface 280 may include a lower recess 282. The lower recess 282 may include a frustoconical surface configured to engage a frustoconical surface of the cam bolt assembly base 620.

Furthermore, the second scissors portion 250 may include a cam bolt hole 265 that passes vertically through the lower handle 260. In one embodiment, the cam bolt hole 265, and the lower recess 282 are coaxially aligned with one another so as to permit the cam bolt 610 to pass through the cam bolt hole 265, the lower recess 282, and the spring 206 engaged with the upper surface 270. To this end, the cam bolt hole 265 may have a diameter greater than a diameter of the cam bolt 610 and the lower recess 282 may have a diameter greater than a diameter of the frustoconical surface of the cam bolt assembly base 620.

The first scissors portion 210 may further include one or more first jaws 212 at an end of the first scissors portion 210 that is distal from the upper handle 220. Similarly, the second scissors portion 250 may include one or more second jaws 252 at an end of the second scissors portion 250 that is distal from the lower handle 260. In the depicted embodiment, the first scissors portion 210 includes two first jaws 212 that interleave with a single second jaw 252 of the second scissors portion 250. However, in other embodiments, the orientations of the jaws 212, 252 may be reversed with two second jaws 252 interleaved with a single first jaw 212. In yet other embodiments, the scissors portions 210, 250 may each include a different quantity jaws 212, 252 than depicted. For example, in some embodiments, the scissors clamp 200 may include 2, 3, 4, 5, etc. first jaws 212 and/or second jaws 252. Regardless of the number of jaws 212, 252, the jaws 212, 252 generally define a clamping passage 290 through which an object such as a frame member, a table post, a retractor handle, etc. may pass. For example, the clamping passage 290 may be sized to accommodate the extension arm 19 of FIG. 2.

Furthermore, distal ends 214, 254 of the jaws 212, 252 may be separated from one another to form a mouth opening 292 to the clamping passage 290. When the joint clamp 100 is in an unlocked position, the scissors clamp 200 may be clipped-on an object via application of a clip-on force that causes the object to pass through the mouth opening 292, passed distal ends 214, 254 of the jaws 212, 252, and into the clamping passage 290. Similarly, when the joint clamp 100 is in an unlocked position, the scissors clamp 200 may be clipped-off or removed from an object via application of a clip-off force that causes the object to move from the clamping passage 290, through the mouth opening 292, and passed distal ends 214, 254 of the jaws 212, 252.

As shown, a pivot pin 216 may pivotally couple the first scissors portion 210 to the second scissors portions 124. In particular, the first scissors portion 210 may include a pivot hole 215 that passes through lateral sides 217 of the first scissors portion 210. Similarly, the second scissors portion 250 may include a pivot hole 255 that passes through lateral sides 257 of the second scissors portion 250. The pivot pin 216 may pass through the pivot holes 215, 255 and pivotally join the first scissors portion 210 to the second scissors portion 250. As a result, the first scissors portion 210 and the second scissors portion 250 may pivot about a longitudinal axis of the pivot pin 216. More specifically, relative movement of the handles 220, 260 with respect to each other translates into relative movement of the jaws 212, 252 with respect to each other. For example, as the handles 220, 260 move closer together, the jaws 212, 252 move closer together. Conversely, as the handles 220, 260 move away from each other, the jaws 212, 252 move away from each other.

As shown, the handles 220, 260 of the scissors clamp 200 are separated by a gap 294. A compressive force applied to the handles 220, 260 may move the handles 220, 260 toward one another thus reducing the gap 294 between the handles 220, 260. Such reduction in the gap 294 causes the scissors portions 210, 250 to rotate about pivot pin 216 thus causing the jaws 212, 252 to move toward each other. Such movement reduces a diameter of the clamping passage 290 formed by the jaws 212, 252 and creates a tighter grip on an object such as a frame member, a table post, a retractor handle, etc. passing through the clamping passage 290.

Figure 4:
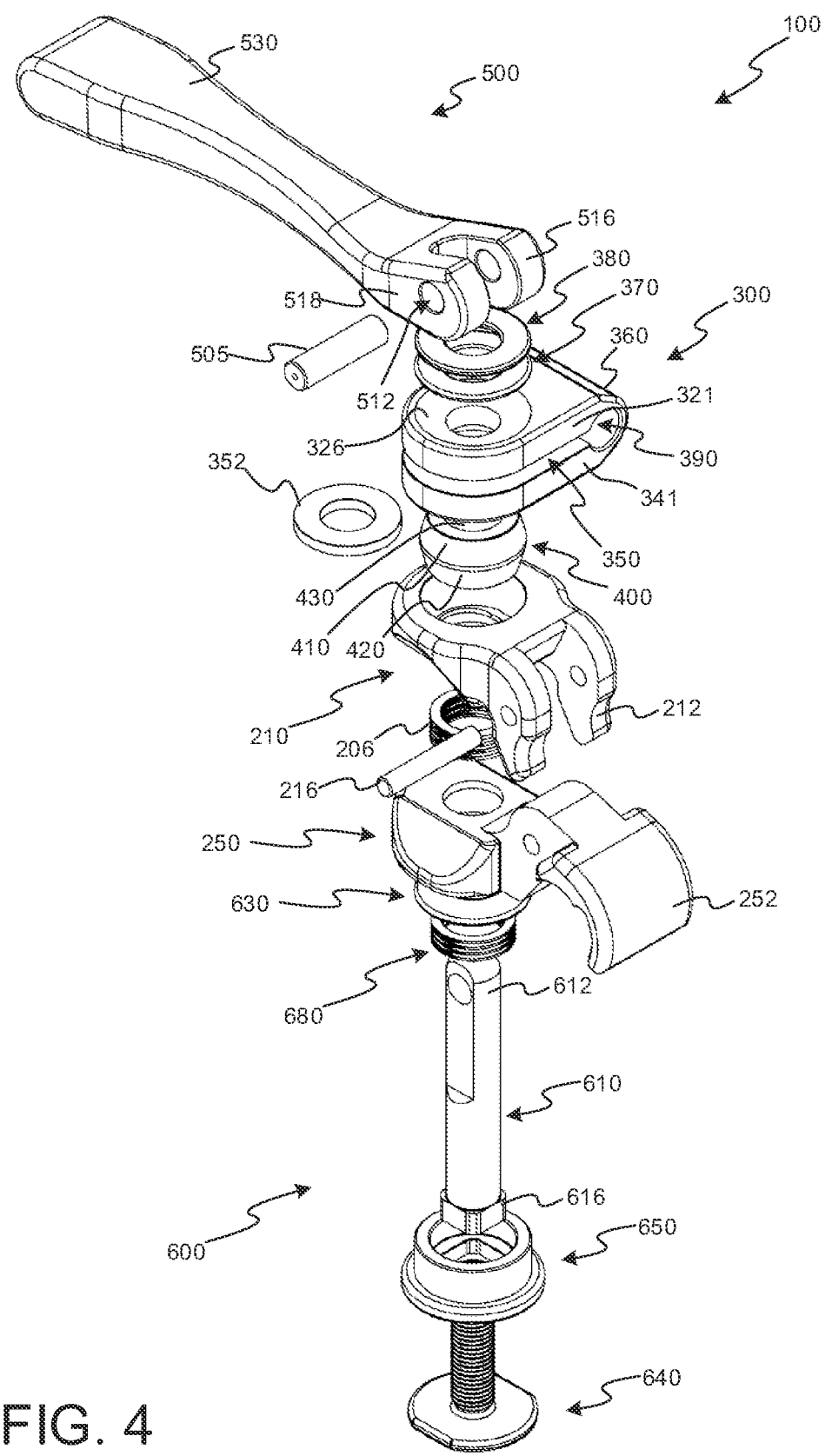
FIG. 4 is a exploded view of the joint clamp shown in FIG. 3.

Turning now to FIGS. 4-6, further details of the circle clamp 300 are provided. In particular, the circle clamp 300 may include an upper portion 320 and a lower portion 340 connected at a fulcrum 360. The upper portion 320 may comprise an upper surface and a lower surface. The upper surface may include a frustoconical recess 326 configured to receive a first washer 370. Furthermore, a cam bolt hole may extend vertically through the recess 326 in the upper surface. The cam bolt hole may have a diameter greater than a diameter of the cam bolt 610 to permit passage of the cam bolt 610 through the upper portion 320. Moreover, a longitudinal axis of the cam bolt hole may be coaxially-aligned with a longitudinal axis of the frustoconical recess 326.

The lower portion 340 may comprise an upper surface and a lower surface. The lower surface may include a frustoconical recess 346 configured a frustoconical surface of the bushing 140. Furthermore, a cam bolt hole may extend vertically through the recess 346 in the lower surface. The cam bolt hole may have a diameter greater than a diameter of the cam bolt 610 to permit passage of the cam bolt 610 through the lower portion 340. Moreover, a longitudinal axis of the cam bolt hole may be coaxially-aligned with a longitudinal axis of the frustoconical recess 346 and the cam bolt hole of the upper portion 320.

The first washer 370 may have a generally cylindrical-shape with a planar upper surface and a frustoconical lower surface. The frustoconical lower surface may be configured to closely mate with the frustoconical recess 326 in the upper surface of the circle clamp 300. As shown, the washer 370 may further include a cam bolt hole that extends through the planar upper surface and the frustoconical lower surface. The cam bolt hole may have a diameter greater than a diameter of the cam bolt 610 so as to permit passage of the cam bolt 610 through the washer 370.

A second washer 380 may be positioned between the first washer 370 and the cam head 510 of the cam lever 500. The second washer 380 may have a generally cylindrical-shape with a planar upper surface and a planar lower surface. The planar lower surface may be configured to closely mate with the planar upper surface of the first washer 370. Similar to washer 370, the washer 380 may include a cam bolt hole that extends through the planar upper surface and the planar lower surface. The cam bolt hole may have a diameter greater than a diameter of the cam bolt 610 so as to permit passage of the cam bolt 610 through the washer 380.

The circle clamp 300 may further include a circular clamping passage 390. The circular clamping passage 390 may pass through lateral sides 321 of the upper portion 320 and lateral sides 341 of the lower portion 340 at a location proximal the fulcrum 360. A longitudinal axis of the clamping passage 390 may be perpendicular to the longitudinal axes of the cam bolt holes through the circle clamp 300. However, in other embodiments, the circle clamp 300 may orient the longitudinal axis of the clamping passage 390 differently with regard to the longitudinal axes of the cam bolt holes through the circle clamp.

The clamping passage 390 may permit an object such as a frame member, a table post, a retractor handle, etc. to pass laterally through the circle clamp 300. For example, the clamping passage 390 may be sized to accommodate the cross bar 18 of FIG. 2. As shown, the circle clamp 300 may include a gap 350 between the lower surface of the upper portion 320 and the upper surface of the lower portion 340. The gap 350 may permit a clamping force to squeeze the circle clamp 300 and tighten a grip on the object passing through the clamping passage 390. In particular, the clamping force may move the upper portion 320 and the lower portion 340 toward one another, thus reducing a circumference or diameter of the clamping passage 390 and constricting the area within clamping passage 390.

A third washer 352 may be positioned in the gap 350 between the lower surface of the upper portion 320 and the upper surface of the lower portion 340. The washer 352 may have a generally cylindrical-shape with a planar upper surface and a planar lower surface. Similar to washer 370, the washer 352 may include a cam bolt hole that extends through the planar upper surface and the planar lower surface. The cam bolt hole may have a diameter greater than a diameter of the cam bolt 610 to permit passage through the washer 352. The washer 352 may prevent the clamping force from reducing the gap 350 beyond the thickness of the washer 352. In this manner, the washer 352 may operate as a governor so as to prevent an application of an excessive gripping force that could potentially damage the object passing through the clamping passage 390 and/or circle clamp 300.

As shown in FIGS. 4-6, the joint clamp 100 may further include a bushing 400 between the scissors clamp 200 and the circle clamp 300. In particular, the bushing 400 may include a frustoconical upper surface 410, a frustoconical lower surface 420, and a cam bolt hole 430. The upper surface 410 may be configured to engage the recess 346 in the lower portion 340 of the circle clamp 300. Similarly, the lower surface 420 may be configured to engage a recess of the scissors clamp 200. The cam bolt hole 430 may pass vertically through the bushing 400 and may have a diameter greater than a diameter of the cam bolt 610 to permit passage of the cam bolt 610 through the bushing 400. A longitudinal axis of the bushing 400 may be coaxial with the longitudinal axis of the cam bolt 610 and the longitudinal axis of the cam bolt hole 430.

The cam lever 500 may include a cam head 510 and a handle 530 connected to the cam head 510. The cam head 510 may be coupled to an upper end 612 of the cam bolt 610 via a pivot pin 505 that passes through pivot holes 512 in the cam head 510 and a pivot hole 614 in an upper end 612 of the cam bolt 610. In particular, the cam head 510 may include two side members 516, 518 that form an interposed channel configured to receive the upper end 612 of the cam bolt 610. Each side member 516, 518 may include a pivot hole 512 that is coaxially aligned with the corresponding pivot hole 512 of the other side member 516, 518. The cam pin 505 may passes through pivot holes 512 in the side member 516, 518 and a pivot hole 614 in an upper end 612 of the cam bolt 610, thus coupling the cam bolt assembly 600 to the cam lever 500.

Figure 3:
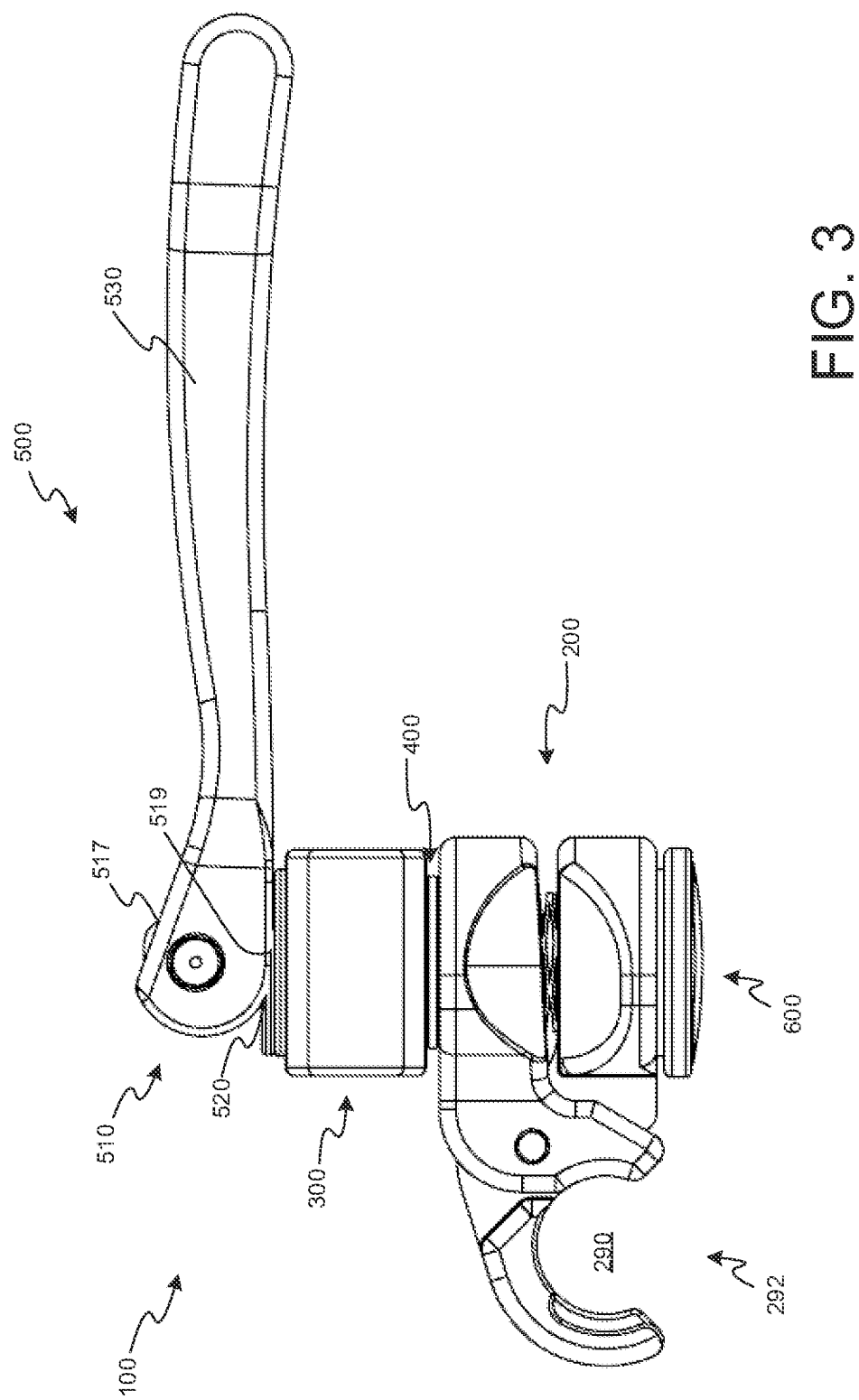
FIG. 3 is a side view of a first embodiment of a joint clamp for the retractor system shown in FIG. 1.

As shown in FIG. 3, an outer edge of the cam head 510 may be eccentric or multi-curved, such that the distance between the pivot pin 505 and the upper surface of the washer 380 increases as the cam lever 500 is moved from its unlocked position of FIG. 6 towards its locked position of FIG. 5. Hence, movement of the cam lever 500 towards its locked position draws the cam bolt 610 upwardly through cam bolt holes in the clamps 200, 300 and compresses the clamps 200, 300 between the outer edge of the cam head 510 and a base 620 of the cam bolt assembly 600. Compression of the resilient clamps 200, 300 constricts the area circumscribed by cylindrical clamping passages 290, 390 to secure clamps 200, 300 to the objects such as frame members, table posts, retractor handles, etc. passing through cylindrical clamping passages 290, 390.

Referring now to FIGS. 3, 5, and 6, planar surface 519 and the eccentric nature of the outer edge serves to help retain the cam lever 500 in the locked position. Because a radial distance between the pivot pin 505 and the planar surface 519 is smaller than the radial distance between the pivot pin 505 and an edge portion 520 proximate the planar surface 519, movement of cam lever 500 from the locked position to the unlocked position requires rotating the cam lever 500 such that the edge portion 520 moves passed the washer 380. Such movement requires drawing the cam bolt assembly base 620 toward the circle clamp 300, thus increasing the compression applied to the clamps 200, 300. As such, the cam lever 500 when in the locked position rests in a local minimum of compression applied to the clamps 200, 330 and thus decreases the likelihood of unintentionally loosening the joint clamp 100 by rotating the cam lever 500 away from its locked position of FIG. 5.

Rotation of cam lever 500 towards its unlocked position moves the cam bolt 610 downwardly through cam bolt apertures in the clamps 200, 300. Due to the downward movement of the cam bolt 610, the base 620 of the cam bolt assembly 600 may be urged away from scissors clamp 300, thus reducing or removing a clamping force applied to resilient clamps 200, 300. When in the unlocked position, the clamps 200, 300 are loosely coupled to the cam lever 500 via the cam bolt assembly 600 and may be rotated relative to one another about a longitudinal axis of the cam bolt 610. The base 620 of the cam bolt assembly 600 may prevent clamps 200, 300 from being slid off a lower end of the cam bolt assembly 600. The removed or reduced compression on clamps 200, 300 may cause cylindrical clamping passages 290, 390 to expand their diameter, allowing clamps 200, 300 to be moved relative to objects such as frame members, table posts, retractor handles, etc. passing through the cylindrical clamping passages 290, 390.

When in the unlocked position, the scissors clamp 200 and the circle clamp 300 are able to rotate with respect to each other. Such rotation provides greater freedom to position attached objects such as frame members, table posts, retractor handles, etc. in a desired manner. The ability to rotate the clamps 200, 300 may be locked or unlocked by the cam lever 500. When the cam lever 500 is in the unlocked position, the scissors clamp 200 and the circle clamp 300 may rotate with respect to each other about a longitudinal axis of the adjustable cam bolt 610. When the cam lever 500 is in the locked position, rotation of the scissors clamp 200 with respect to the circle clamp 300 is made extremely difficult, with the result establishing a fixed position for the clamps 200, 300 with respect to each other so long as the cam lever 500 is in the locked position. As the cam lever 500 is rotated into the locked position, the first scissors portion 210 of the scissors clamp 200 is pressed against the bushing 400 with greater force, and the lower portion 340 of the circle clamp 300 is also pressed against the bushing 400 with greater force. This greater force creates greater friction between the scissors clamp 200 and the bushing 400 and between the circle clamp 300 and the bushing 400, greatly restricting the ability of the scissors clamp 200 and the circle clamp 300 to rotate with respect to each other.

Details regarding the cam bolt assembly 600 are provided with reference to FIGS. 4-9. As shown, the cam bolt assembly 600 includes a cam bolt 610 coupled to a cam bolt assembly base 620. The base 620 comprises a washer 630, a set screw 640, a sleeve 650, and a compression spring 680.

The washer 630 may have a generally cylindrical-shape with a frustoconical upper surface and a planar lower surface. The upper surface may be configured to closely mate with the recess 282 in the lower handle 260 of the scissors clamp 200. The lower surface may be configured to engage an upper end of the compression spring 680. The lower surface may further engage the keyed sleeve 650 when the cam lever 500 is in the locked position. As shown, the washer 630 may further include a cam bolt hole that extends through the upper surface and the lower surface. The cam bolt hole may have a diameter greater than a diameter of the cam bolt 610 to permit passage of the cam bolt 610 through the washer 630 and the spring 680 seated against the lower surface of the washer 630.

An upper end 612 of the cam bolt 610 may include a pivot pin hole 614 through which pivot pin 505 may pass and couple the cam head 510 to the cam bolt 610. A lower end 616 of the cam bolt 610 may be keyed to engaged a keyed recess 652 of the sleeve 650. The cam bolt 610 may further include a threaded bore 618 that extends longitudinally into the lower end 616. The threaded bore 618 may be sized to receive a thread shaft 644 that extends from a head 642 of the set screw 640. The threads of the threaded bore 618 may engage threads of the threaded shaft 644 and draw the head 642 toward the cam bolt 610 when the set screw 640 is turned in a first direction with respect to the cam bolt 610 and move the head 642 away from the cam bolt 610 when the set screw is turn in a second direction opposite the first direction.

The sleeve 650 may have generally cylindrical shape with a circular upper surface 660 and a circular lower surface 670. In particular, the sleeve 650 may include a cavity 662 that extends into the upper surface 660, but not all the way through to the lower surface 670. The cavity 662 may have a diameter greater than the diameter of the spring 680. The cavity 662 may receive a lower end of the spring 680 and a bottom surface 664 of the cavity 662 may engage the lower end of the spring 680.

The sleeve 650 may include a keyed recess 652 in the bottom surface 664 of the cavity 662. The lower end 616 of the cam bolt 610 and the keyed recess 652 are sized such that the keyed outer surface of lower end 616 closely mates with an inner surface of the keyed recess 652 when the lower end 616 of the cam bolt 610 is received by the keyed recess 652. In one embodiment, the lower end 616 of the cam bolt 610 may include a keyed outer surface with a cross-section that is square-shaped with chamfered corners. Likewise, keyed recess 652 of the sleeve 650 may have a keyed inner surface with a cross-section that is square-shaped with chamfered corners that closely mates with the keyed outer surface of the cam bolt 610. Such engagement of the cam bolt 610 with the keyed recess 652 rotationally locks the sleeve 650 to the cam bolt 610. In particular, the keyed engagement ensures that the sleeve 650 rotates in unison with the cam bolt 610 about its longitudinal axis.

The lower surface 670 of the sleeve 650 may include a recess 672. The recess 672 may have a diameter greater than a diameter of the head 642 of the set screw 640. A set screw hole 674 may extend vertically through the lower surface 670 of the sleeve 650 and through the bottom surface 664 of the cavity 662. The set screw hole 674 may have a diameter greater than a diameter of the thread shaft 644 of the set screw 640. A longitudinal axis of the set screw hole 674 may be coaxially aligned with the cam bolt 610 and its threaded bore 618 when the lower end 616 of the cam bolt 610 is engaged with the sleeve 650.

The bottom surface 664 of the cavity 662 provides a surface upon which the spring 680 rests. The spring 680, among other things, may generally prevent the washer 630 from sliding down the cam bolt 610 when in the unlocked position.

The set screw 640 includes the head 642 and the shaft 644 that extends from head 642. The shaft 644 includes threads which engage threads along an inner surface of the bore 618. In particular, the shaft 644 may pass through the recess 672, through the set screw hole 374, and into threaded bore 618 of the cam bolt 610.

In some embodiments, a depth of the recess 672 is greater than the thickness of the head 642. In such embodiments, the head 642 of the set screw 640 does not extend beyond the lower surface 670 of the sleeve 650, thus preventing unauthorized personnel from rotating the set screw 640 with respect to the cam bolt 610 after assembly. In some embodiments, a depth of the recess 672 is greater than or nearly greater than a side wall thickness of the head 642. In such embodiments, a surface of the head 642 may extend beyond the lower surface 670 of the sleeve 650, but the sleeve 650 may cover or substantially cover the side walls of the head 642. By covering or substantially covering the side walls, unauthorized personnel may be unable to rotate the set screw 640 with respect to the cam bolt 610 after assembly. In this manner the recessed sleeve 650 may prevent tampering or inadvertent adjustment of the set screw 640 after calibration and assembly.

Due to the engagement of threads, tightening the set screw 640 draws the set screw 640 into the bore 618 and increases a compression force on the clamps 200, 300 and thus their respective clamping forces on objects passing through their clamping passages 290, 390. Conversely, loosening the set screw 640 draws the set screw 640 from the bore 618 and decreases the compression force on the clamps 200, 300 and thus their respective clamping forces on objects passing through their respective clamping passages 290, 390.

The depth of the keyed recess 652 may establish a range of adjustment provided by the set screw 640. In particular, the set screw 640 may be tightened (e.g., rotated in a first direction) until the lower end 616 of the cam bolt 610 is drawn flush against the a bottom surface of the recess 652. Conversely, the lower end 616 preferably remains at least partially within the recess 652 to maintain the rotationally locked engagement between the cam bolt 610 and the sleeve 650. Thus, the set screw 640 may be loosened (e.g., rotated in a second direction opposite the first direction) until just before the lower end 616 of the cam bolt 610 is drawn completely from the recess 652. While the depth of the recess 652 may limit the range of adjustment, the set screw 640 may provide a continuous adjustments within the range.

In some embodiment, the set screw 640 may be further affixed to the cam bolt 610 and/or the sleeve 650 to further ensure the set screw 640 does not rotate with respect to the cam bolt 610 after the set screw 640 has been placed at the desired setting. For example, an epoxy, adhesive, and/or other affixing material may be applied to threads of the set screw 640 and/or bore 618. After such affixing material dries, cures, sets, etc., the affixing material may affix the set screw 640 to the cam bolt 610 and help prevent the set screw 640 from rotating with respect to the cam bolt 610.

Furthermore, the set screw 640 may be affixed to the sleeve 650. For example, after appropriately adjusting the clamping force via the set screw 640, the set screw 640 may be welded (e.g., tack welded) to the sleeve 650 to lock the set screw 640 in place. However, the set screw 640 may be affixed via other techniques such as applying affixing materials (e.g., epoxies, adhesives, solders, etc.) and/or using other welding techniques.

As noted above, the engagement of the cam bolt 610 with the sleeve 650 may ensure that the cam bolt 610 and the sleeve 650 rotate in unison. By affixing the set screw 640 to the sleeve 650, the cam bolt 610, the sleeve 650, and the set screw 640 likewise rotate in union. In this manner, a rotating cam bolt 610 and sleeve 650 may be prevented from applying torque to the set screw 640 that could otherwise tighten or loosen the set screw 640 with respect to the cam bolt 610.

Figure 12:
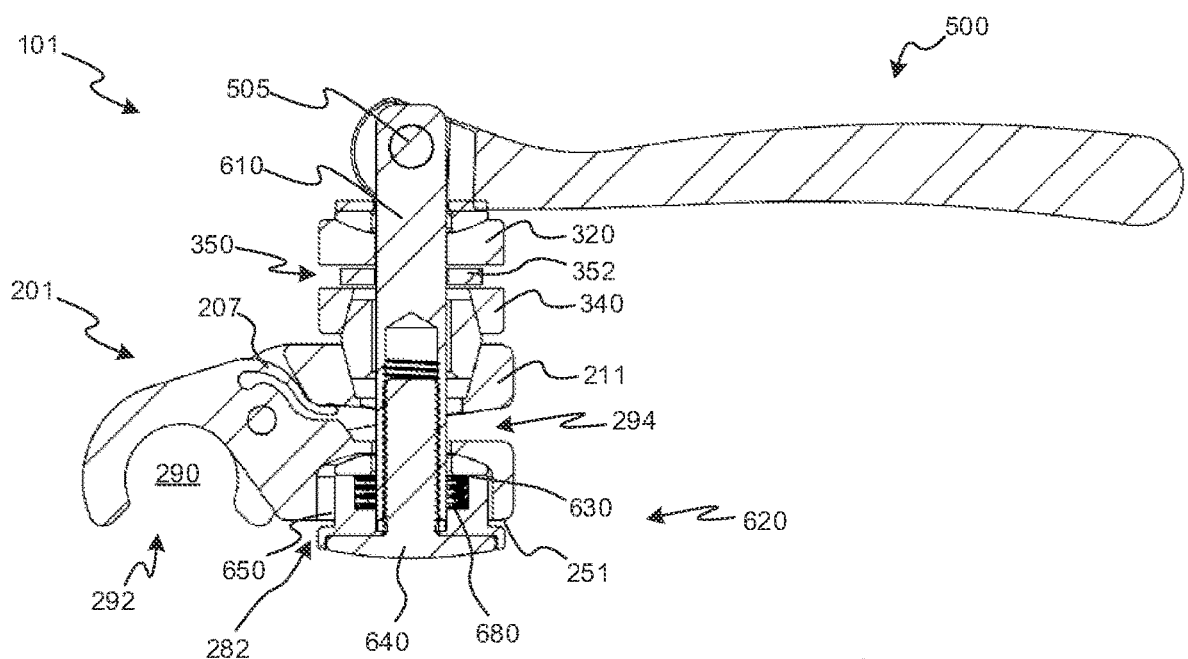
FIG. 12 is a cross-sectional view of a second embodiment of joint clamp with its cam lever in a locked position.
Figure 13:
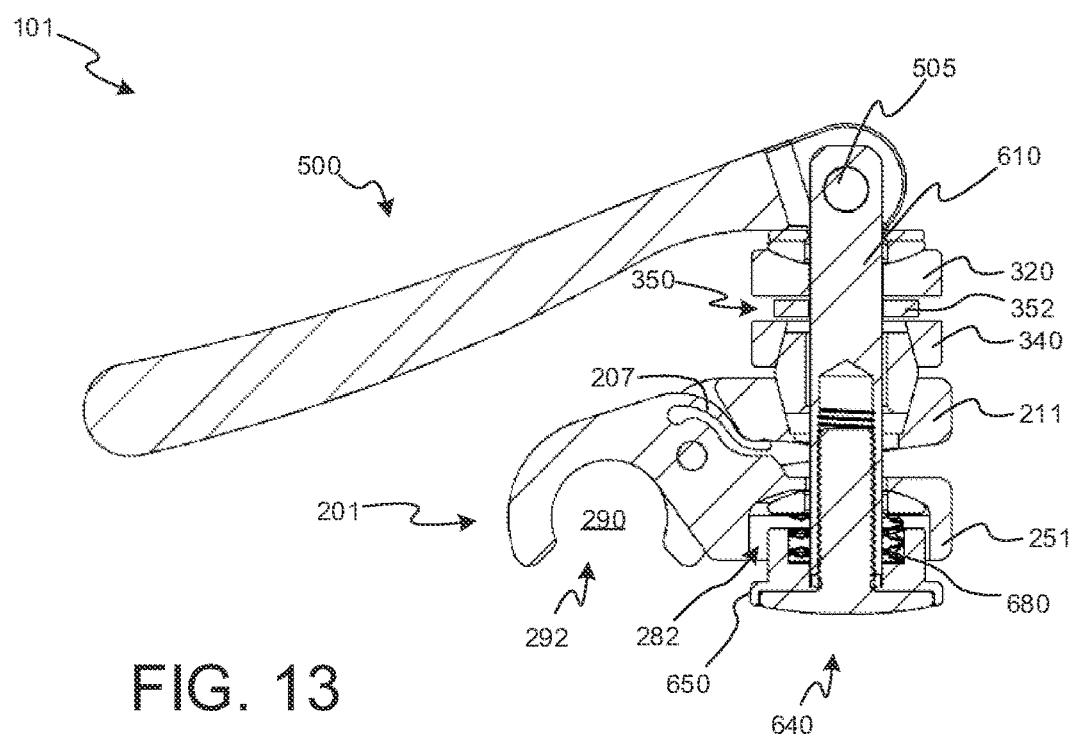
FIG. 13 is a cross-sectional view of the second embodiment of joint clamp with its cam lever in an unlocked position.
Figure 14:
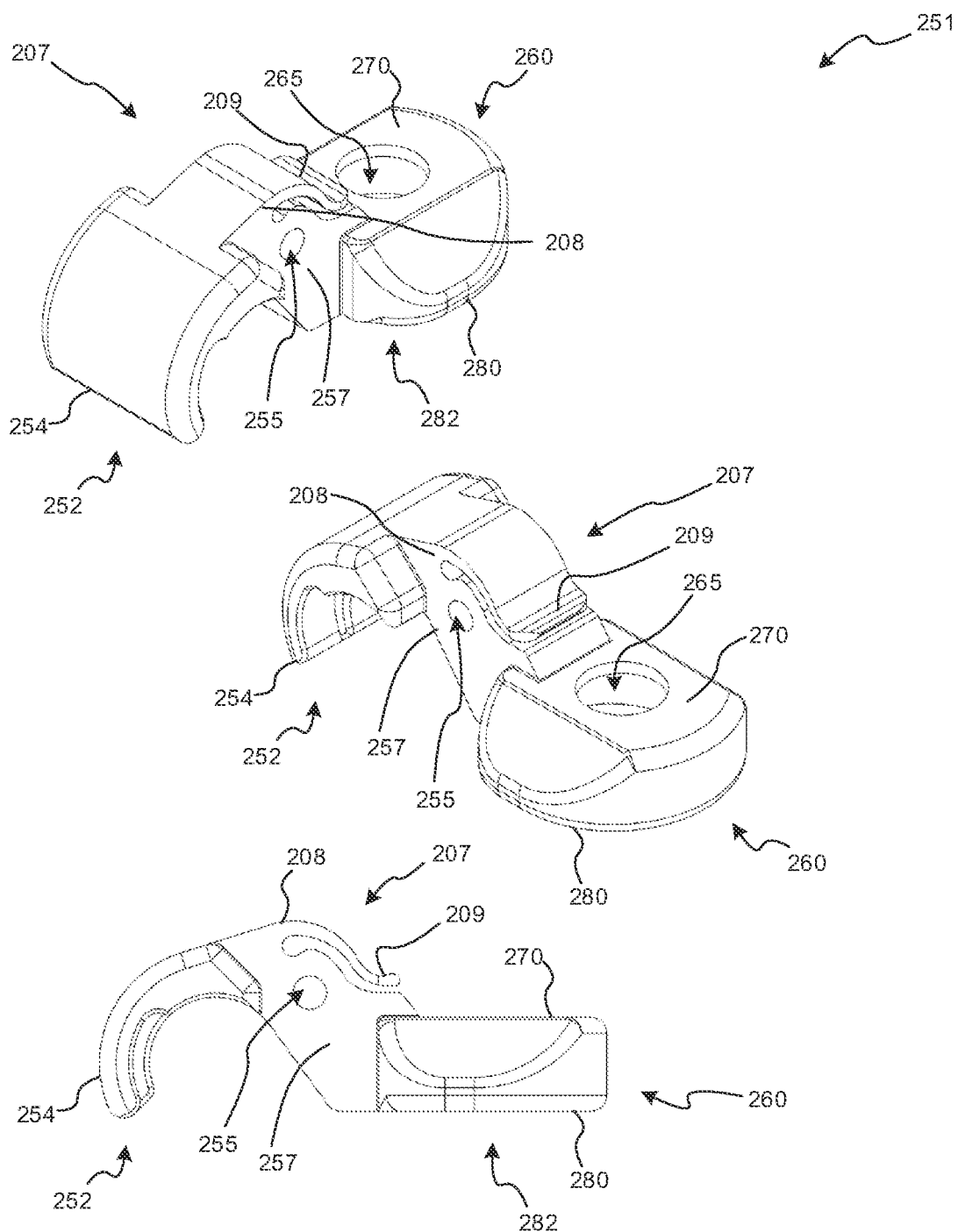
FIG. 14 depicts multiple views of a second scissors portion of the joint clamp shown in FIGS. 12 and 13.
Figure 15:
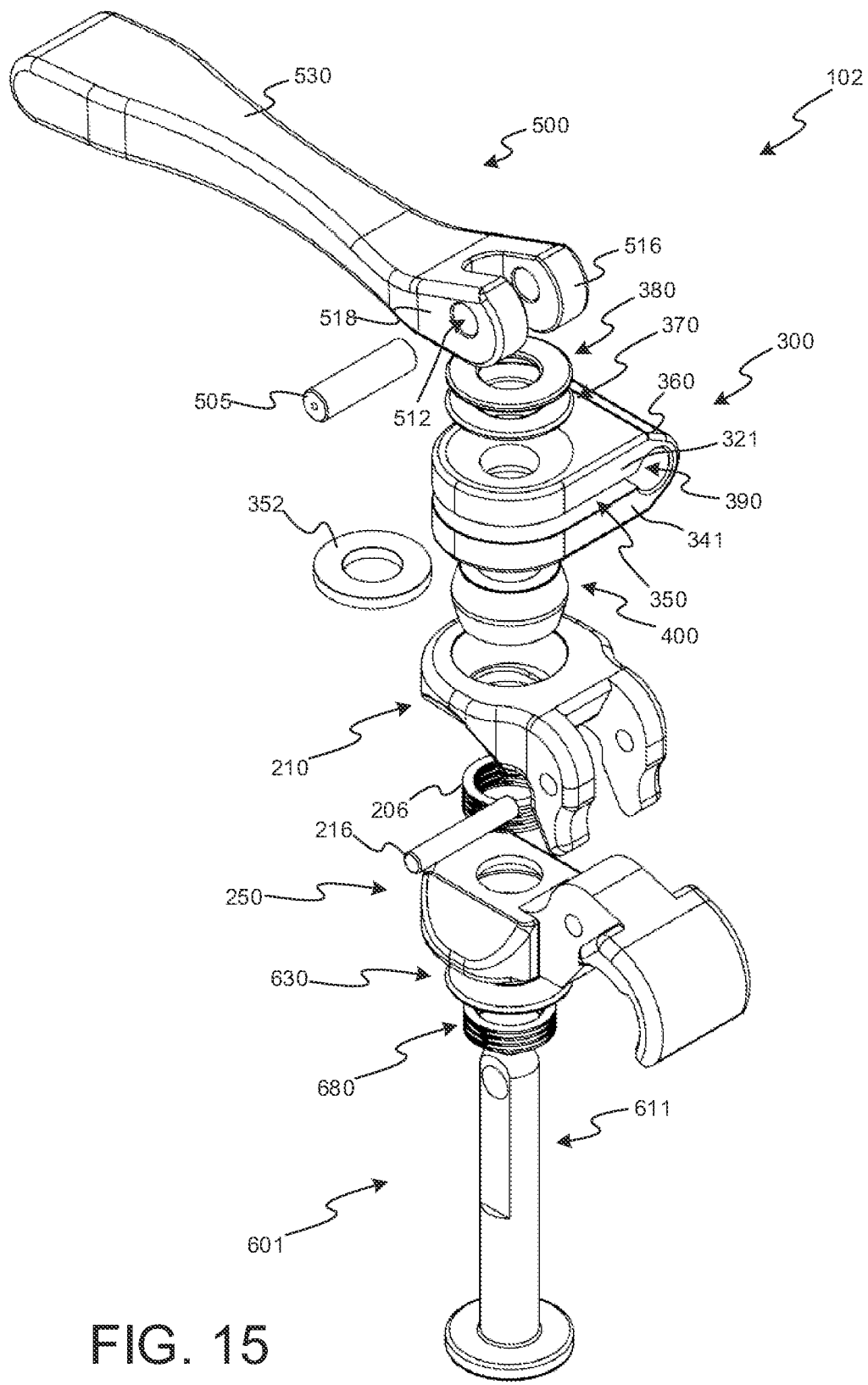
FIG. 15 is a exploded view of a third embodiment of the joint clamp.

Referring now to FIGS. 12-14, a second embodiment of a joint clamp 101 is shown. The joint clamp 101 and the joint clamp 100 shown in FIGS. 3-11 are implemented in a similar manner. However, the scissors clamp 201 of the joint clamp 101 differs from the scissors clamp 200 of the joint clamp 100. In particular, the scissors clamp 201 includes cantilever spring 207 instead of the compression spring 206 of the scissors clamp 200. The cantilever spring 207 has a greater spring constant than the spring 680 and is thus stiffer than the spring 680. As such, the cantilever spring 207 functions similarly to the compression spring 206 in that the compression spring 206 biases the jaws 212, 252 in an open direction, but reaches an uncompressed or resting state before opening the jaws 212, 252 beyond a receiving or partially-opened position as explained above.

As shown, the first scissors portion 211 and the second scissors portion 251 of the scissors clamp 201 may be implemented in essentially the same manner as the first scissors portion 210 and the second scissors portion 250 of the scissors clamp 200. However, since the scissors clamp 201 lacks the compression spring 206, the first scissors portion 211 may be implemented without the lower recess 242 of the scissors clamp 200. Furthermore, the second scissors portion 251 may include the cantilever spring 207. In the depicted embodiment, the cantilever spring 207 is integrally formed in the second scissors portion 251. However, in some embodiments, the cantilever spring 207 may be a separate piece that engages the first scissors portion 211 and the second scissors portion 251 in a similar manner as the integrated cantilever spring 207.

As shown, the cantilever spring 207 includes a first end 208 coupled to an upper surface of the second scissors portion 251 and a second end 209 that engages a lower surface of the first scissors portion 211. As shown, the first end 208 and the second end 209 of the cantilever spring 207 lie on opposite sides of the pivot hole 255 of the second scissors portion 251. As such, when in the unlocked position of FIG. 13, the cantilever spring 207 may maintain a desired gap between the handles 220, 260 and thus a partially-opened mouth opening 292. As such, similar to the first scissors clamp 200, a clip-on and clip-off force of the first scissors clamp 201 is generally defined by the spring 680.

Referring now to FIGS. 15-19, a third embodiment of a joint clamp 102 is shown. The joint clamp 102 and the joint clamp 100 shown in FIGS. 3-11 are implemented in a similar manner. However, the cam bolt assembly 601 of the joint clamp 102 differs from the cam bolt assembly 600 of the joint clamp 100. As shown, the cam bolt assembly comprises a cam bolt 611 and a base 621. The cam bolt 611 may be implemented similarly to the cam bolt 610. However, the lower end 617 of the cam bolt 611 is not keyed or bored, but integrally coupled to the base 621.

In particular, the base 621 includes a washer 630, a spring 680, a spring container 700, and a foot 710. The washer 630 and the spring 680 of the base 621 may be implemented in essentially the same manner as the washer 630 and spring 680 of the base 620. The foot 710 may be generally cylindrical in shape with an upper surface 712 and a lower surface 714. The upper surface 712 may be coupled to the lower end 617 of the cam bolt 611. In one embodiment, the cam bolt 611 and the foot 710 are integrally formed. Thus, similar to the cam bolt 610 and the set screw 640 of the cam bolt assembly 600, the cam bolt 611 and the foot 710 may rotate in unison about a longitudinal axis of the cam bolt 611.

The spring container 700 may comprises an upper surface 702, a lower surface 704, and a hole 706 through the upper surface 702 and the lower surface 704. The lower surface 704 may engage the upper surface 712 of the foot 710. A diameter of the hole 706 may be greater than a diameter of the spring 680 to permit passage of a lower end of the spring 680 through the spring container 700. As such, a lower end of the spring 680 may engage the upper surface 712 of the foot 710. The upper end of the spring 680 may engage a lower surface of the washer 630 as described above with regard to the cam bolt assembly 600.

Figure 16:
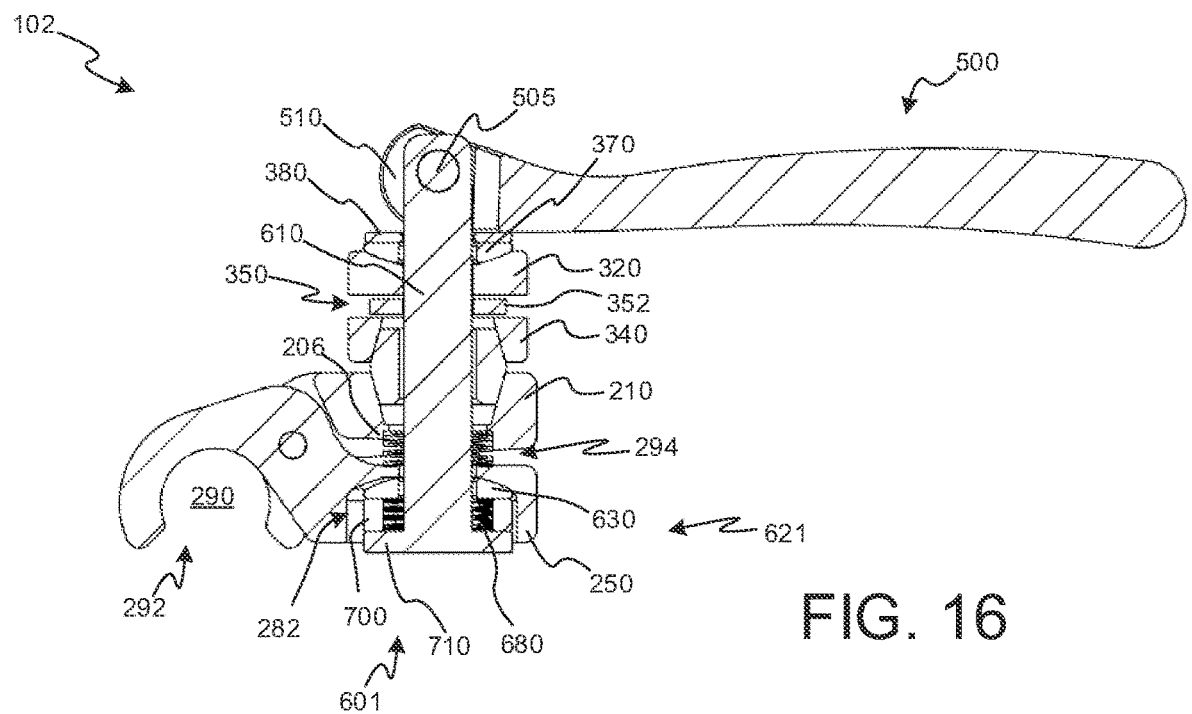
FIG. 16 is a cross-sectional view of the joint clamp shown in FIG. 15 with its cam lever in a locked position.
Figure 17:
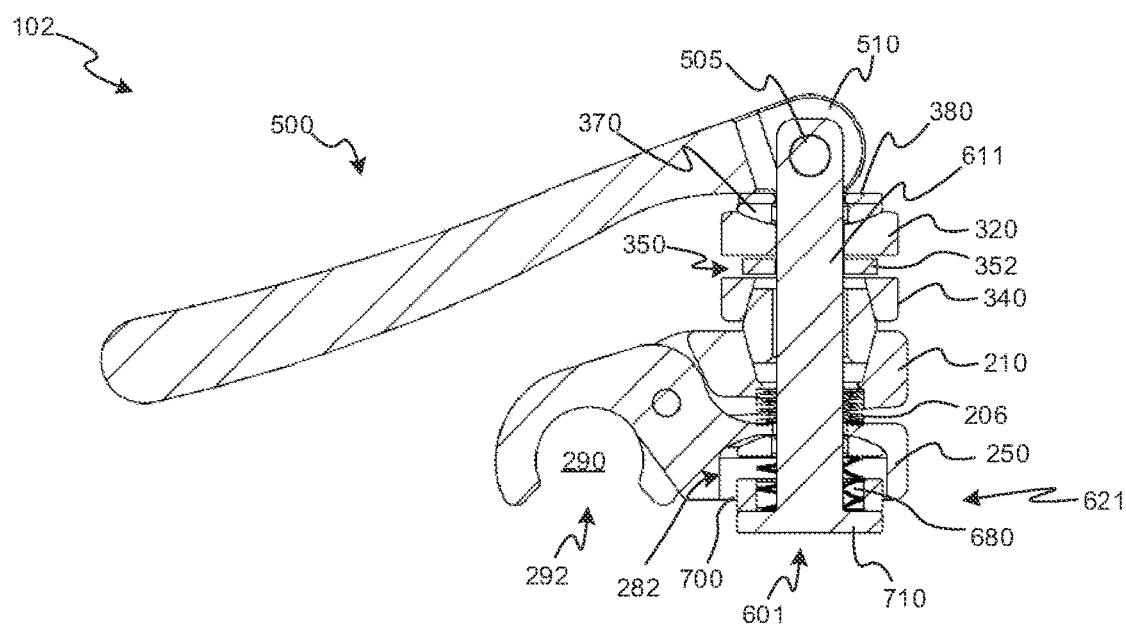
FIG. 17 is a cross-sectional view of the joint clamp shown in FIG. 15 with its cam lever in an unlocked position.
Figure 18:
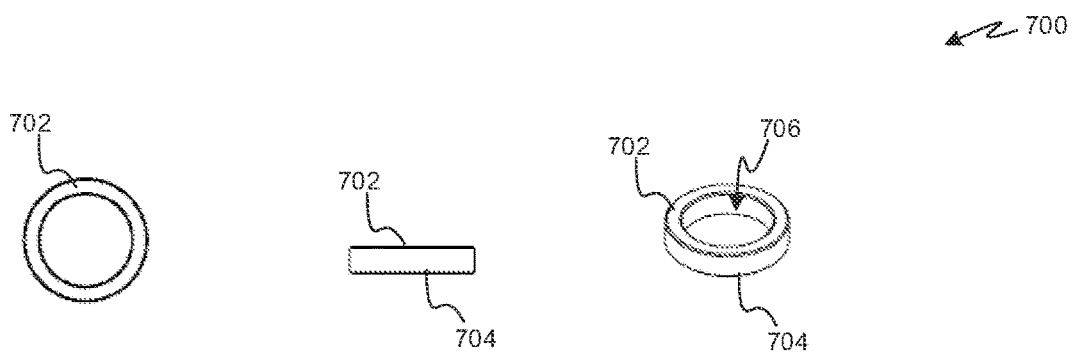
FIG. 18 depicts multiple views of a spring container of the joint clamp shown in FIG. 15.
Figure 19:
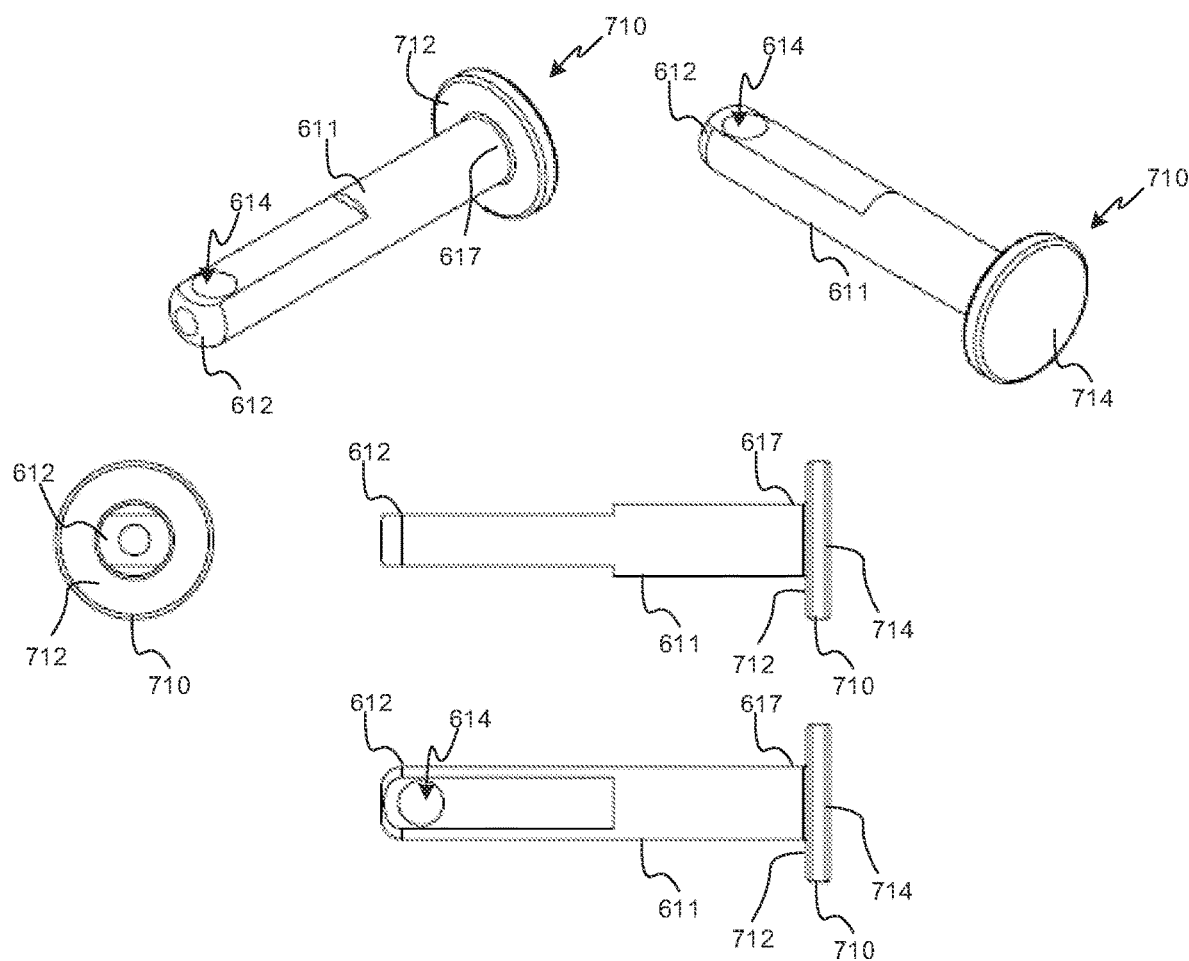
FIG. 19 depicts multiple views of a cam bolt of the joint clamp shown in FIG. 15.

As shown in FIG. 16, when the joint clamp 102 is in a locked position, the upper surface 702 of the spring container 700 engages the lower surface of the washer 630. Moreover, the lower surface 704 of the spring container 700 engages the upper surface 712 of the foot 710. A thickness of the spring container 700 between the upper surface 702 and the lower surface 704 partially specifies a distance between an upper surface of the base 621 and a lower surface of the cam head 510. Similarly, a thickness of the second washer 380 between the cam head 510 and first washer 370 partially specifies the distance between the upper surface of the base 621 and the lower surface of the cam head 510. As explained above, the distance between the upper surface of the base 621 and the lower surface of the cam head 510 specifies the compression force applied to the clamps 200, 300 and thus specifies their respective clamping forces. Accordingly, during a calibration process, spring containers 700 and/or second washers 380 with different thickness may be swapped till a spring container 700 and/or second washer 380 that result in a desired compression force is found. In one embodiment, the thickness of the spring container 700 is maintained at a fixed thickness and calibration of the desired compression force is achieved via a second washer 380 of the appropriate thickness.

Figure 20:
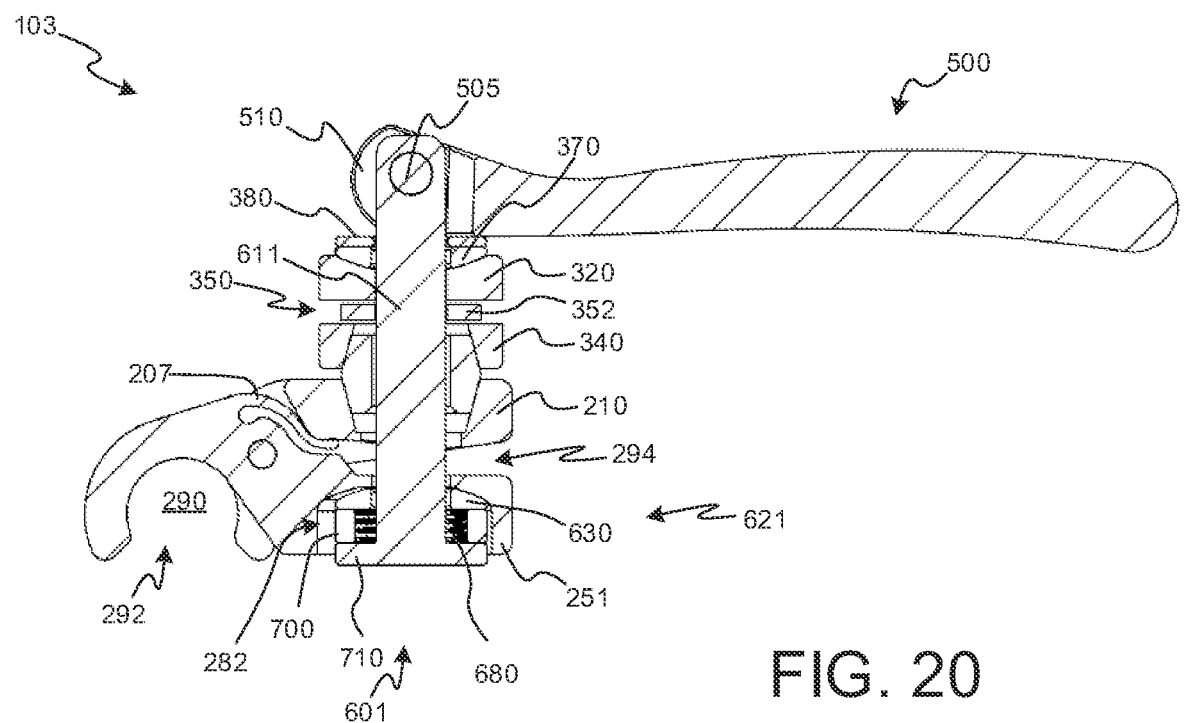
FIG. 20 is a cross-sectional view of a fourth embodiment of the joint clamp with its cam lever in a locked position.
Figure 21:
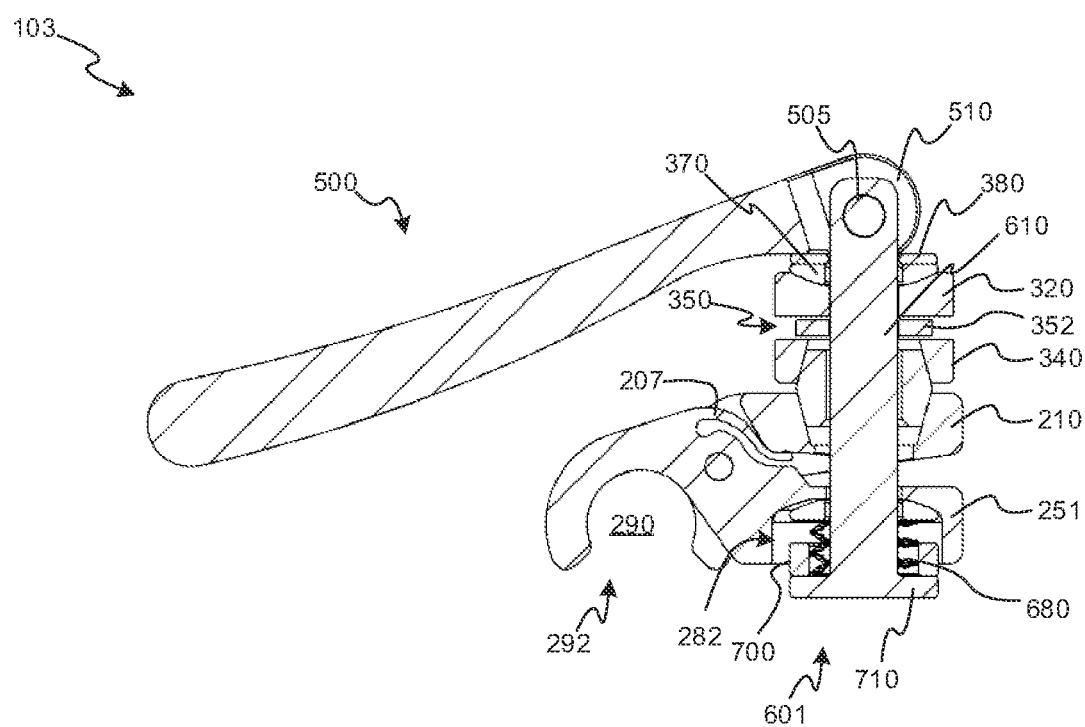
FIG. 21 is a cross-sectional view of the joint clamp shown in FIG. 20 with its cam lever in an unlocked position.

Finally, FIGS. 20-21 depict a fourth embodiment of a joint clamp 103. The joint clamp 103 utilizes a cantilever spring 207 of the joint clamp 101 shown in FIGS. 12-14 and utilizes the cam bolt assembly 601 of the joint clamp 102 shown in FIGS. 15-19. As such, the joint clamp 103 operates in a similar manner as joint clamps 101, 102.

While particular embodiments of the invention have been shown, the invention is not limited thereto since modifications may be made by those skilled in the art, particularly in light of the foregoing teaching. It is, therefore, the appended claims which define the true spirit and scope of the invention.

What is claimed is:

1. A clamp comprising:
    a first scissors portion comprising a first scissors portion handle, a first scissors portion jaw, a first scissors portion first side, and a first scissors portion second side that is opposite the first scissors portion first side;
    a second scissors portion comprising a second scissors portion handle, a second scissors portion jaw, a second scissors portion first side, and a second scissors portion second side that is opposite the second scissor portion first side;
    a first spring that biases the first scissors portion jaw away from the second scissors portion jaw;
    a second spring that biases the first scissors portion jaw toward the second scissors portion jaw;
    a bolt that passes through the first scissors portion handle and the second scissors portion handle, wherein the bolt draws the second scissors portion handle toward the first scissors portion handle and impart a clamping force between the first scissors portion jaw and the second scissors portion jaw;
    wherein between the first scissors portion handle and the second scissors portion handle, the first scissors portion second side faces the second scissors portion first side; and
    wherein between the first scissors portion jaw and the second scissors portion jaw, the first scissors portion first side faces the second scissors portion second side.

2. The clamp of claim 1, wherein a pivot between the first scissors portion handle and the first scissors portion jaw and between the second scissors portion handle and the second scissors portion jaw couples the first scissors portion to the second scissors portion.

3. The clamp of claim 1, comprising:
    a lever coupled to a first end of the bolt; and
    wherein rotation of the lever draws a second end of the bolt toward the second scissors portion handle to impart the clamping force between the first scissors portion jaw and the second scissors portion jaw.

4. The clamp of claim 1, wherein the first spring has a greater spring constant than the second spring.

5. The clamp of claim 1, wherein the first spring includes a cantilever spring comprising a cantilever spring first end coupled to the second scissors portion first side and a cantilever spring second end engaged with the first scissors portion second side.

6. The clamp of claim 1, wherein the first spring reaches a resting position before a gap between the first scissors portion jaw and the second scissors portion jaw increases beyond a diameter of an object encircled by the first scissors portion jaw and the second scissors portion jaw.

7. The clamp of claim 6, wherein the second spring sets a clip-on force used to pass the object through the gap between the first scissors portion jaw and the second scissors portion jaw.

8. The clamp of claim 1, comprising:
a washer between an end of the bolt and the second scissors portion handle; and
wherein the second spring is positioned between the washer and the end of the bolt and applies a spring force to the washer that biases the second scissors portion handle away from the end of the bolt.

9. The clamp of claim 8, comprising:
a spring container between the end of the bolt and the washer; and
wherein the second spring is positioned within a hole of the spring container.

10. The clamp of claim 8, comprising:
a sleeve between the end of the bolt and the washer; and
wherein the second spring is positioned in a cavity of the sleeve with a second spring first end engaging the washer and a second spring second end engaging a cavity surface.

11. The clamp of claim 10, comprising:
a screw that extends through the sleeve and into the end of the bolt;
wherein the cavity surface comprises a keyed recess; and
wherein the end of the bolt comprises a keyed surface engaged with the keyed recess of the cavity surface.

12. The clamp of claim 11, wherein rotation of the screw with respect to the end of the bolt adjusts the clamping force between the first scissors portion jaw and the second scissors portion jaw.

13. A system, comprising:
a longitudinal member having a diameter; and
a clamp comprising a first scissors portion, a second scissors portion, a first spring, a second spring, and a bolt that passes through the first scissors portion and the second scissors portion;
wherein the first scissors portion comprises a first scissors portion jaw;
wherein the second scissors portion comprises a second scissors portion jaw;
wherein the first spring biases the first scissors portion jaw away from the second scissors portion jaw;
wherein the second spring biases the first scissors portion jaw toward the second scissors portion jaw;
wherein the first scissors portion jaw and the second scissors portion jaw engage the longitudinal member around the diameter; and
wherein the first spring reaches a resting position before a gap between the first scissors portion jaw and the second scissors portion jaw increases beyond the diameter of the longitudinal member.

14. The system of claim 13 wherein the second spring sets a clip-off force used to extract the longitudinal member from the clamp via the gap between the first scissors portion jaw and the second scissors portion jaw.

15. The system of claim 13, comprising:
a lever coupled to a first end of the bolt; and
wherein rotation of the lever draws a second end of the bolt toward the second scissors portion to impart a clamping force to the longitudinal member via the first scissors portion jaw and the second scissors portion jaw.

16. The system of claim 13, wherein the first spring has a greater spring constant than the second spring.

17. The system of claim 13, wherein:
the first scissors portion comprises a first scissors portion first side and a first scissors portion second side that is opposite the first scissors portion first side;
the second scissors portion comprises a second scissors portion first side and a second scissors portion second side that is opposite the second scissors portion first side; and
the first spring includes a cantilever spring comprising a cantilever spring first end coupled to the second scissors portion first side and a cantilever spring second end engaged with the first scissors portion second side.

18. The system of claim 13, wherein:
the clamp comprises a washer between an end of the bolt and the second scissors portion handle; and
the second spring is positioned between the washer and the end of the bolt and applies a spring force to the washer that biases the second scissors portion handle away from the end of the bolt.

19. The system of claim 18, wherein:
the clamp comprises a sleeve between the end of the bolt and the washer; and
the second spring is positioned in a cavity of the sleeve with a second spring first end engaging the washer and a second spring second end engaging a cavity surface;
the cavity surface comprises a keyed recess; and
the end of the bolt comprises a keyed surface engaged with the keyed recess of the cavity surface.

20. A clamp comprising:
a first scissors portion comprising a first scissors portion handle and a first scissors portion jaw;
a second scissors portion comprising a second scissors portion handle and a second scissors portion jaw;
a first spring that biases the first scissors portion jaw away from the second scissors portion jaw;
a second spring that biases the first scissors portion jaw toward the second scissors portion jaw, wherein the first spring has a greater spring constant than the second spring; and
a bolt that passes through the first scissors portion handle and the second scissors portion handle, wherein the bolt draws the second scissors portion handle toward the first scissors portion handle and impart a clamping force between the first scissors portion jaw and the second scissors portion jaw.

21. The clamp of claim 20, wherein a pivot between the first scissors portion handle and the first scissors portion jaw and between the second scissors portion handle and the second scissors portion jaw couples the first scissors portion to the second scissors portion.

22. The clamp of claim 20, comprising:
a lever coupled to a first end of the bolt; and
wherein rotation of the lever draws a second end of the bolt toward the second scissors portion handle to impart the clamping force between the first scissors portion jaw and the second scissors portion jaw.

23. The clamp of claim 20, wherein:
the first scissors portion comprises a first scissors portion first side and a first scissors portion second side that is opposite the first scissors portion first side;

the second scissors portion comprises a second scissors portion first side and a second scissors portion second side that is opposite the second scissors portion first side; and the first spring includes a cantilever spring comprising a cantilever spring first end coupled to the second scissors portion first side and a cantilever spring second end engaged with the first scissors portion second side.

24. The clamp of claim 20, wherein the first spring reaches a resting position before a gap between the first scissors portion jaw and the second scissors portion jaw increases beyond a diameter of an object encircled by the first scissors portion jaw and the second scissors portion jaw.

25. The clamp of claim 24, wherein the second spring sets a clip-on force used to pass the object through the gap between the first scissors portion jaw and the second scissors portion jaw.

26. The clamp of claim 20, comprising:
a washer between an end of the bolt and the second scissors portion handle; and
wherein the second spring is positioned between the washer and the end of the bolt and applies a spring force to the washer that biases the second scissors portion handle away from the end of the bolt.

27. The clamp of claim 26, comprising:
a spring container between the end of the bolt and the washer; and
wherein the second spring is positioned within a hole of the spring container.

28. The clamp of claim 26, comprising:
a sleeve between the end of the bolt and the washer; and
wherein the second spring is positioned in a cavity of the sleeve with a second spring first end engaging the washer and a second spring second end engaging a cavity surface.

29. The clamp of claim 28, comprising:
a screw that extends through the sleeve and into the end of the bolt;
wherein the cavity surface comprises a keyed recess; and
wherein the end of the bolt comprises a keyed surface engaged with the keyed recess of the cavity surface.

30. The clamp of claim 29, wherein rotation of the screw with respect to the end of the bolt adjusts the clamping force between the first scissors portion jaw and the second scissors portion jaw.

\* \* \* \* \*